(12) United States Patent
Grenier et al.

(10) Patent No.: US 8,895,053 B2
(45) Date of Patent: Nov. 25, 2014

(54) TESTOSTERONE FORMULATIONS

(75) Inventors: Arnaud Grenier, Steinbrunn le haut (FR); Dario N. Carrara, Oberwil (CH)

(73) Assignee: Ferring B.V., Hoofddorp (NL)

( * ) Notice: Subject to any disclaimer, the term of this patent is extended or adjusted under 35 U.S.C. 154(b) by 0 days.

(21) Appl. No.: 13/979,881

(22) PCT Filed: Jan. 18, 2012

(86) PCT No.: PCT/EP2012/050695
§ 371 (c)(1),
(2), (4) Date: Jul. 30, 2013

(87) PCT Pub. No.: WO2012/101016
PCT Pub. Date: Aug. 2, 2012

(65) Prior Publication Data
US 2013/0295166 A1 Nov. 7, 2013

Related U.S. Application Data

(60) Provisional application No. 61/436,207, filed on Jan. 26, 2011.

(30) Foreign Application Priority Data

Jan. 26, 2011 (EP) .................................... 11152210

(51) Int. Cl.
| | | |
|---|---|---|
| A61K 9/70 | (2006.01) | |
| A61K 47/10 | (2006.01) | |
| A61K 31/568 | (2006.01) | |
| A61K 9/00 | (2006.01) | |

(52) U.S. Cl.
CPC .............. *A61K 31/568* (2013.01); *A61K 47/10* (2013.01); *A61K 9/0014* (2013.01)
USPC ........................... 424/449; 514/177; 514/10.2

(58) Field of Classification Search
CPC ......... A61K 9/06; A61K 9/08; A61K 9/0014; A61K 31/568; A61K 47/10; C07J 5/00
See application file for complete search history.

(56) References Cited

U.S. PATENT DOCUMENTS

| | | |
|---|---|---|
| 3,773,919 A | 11/1973 | Boswell |
| 5,506,207 A | 4/1996 | Rivier et al. |
| 5,516,887 A | 5/1996 | Deghenghi |
| 5,595,760 A | 1/1997 | Cherif-Cheikh |
| 5,821,230 A | 10/1998 | Jiang et al. |
| 5,860,957 A | 1/1999 | Jacobsen et al. |
| 5,863,549 A | 1/1999 | Tarantino |
| 5,925,730 A | 7/1999 | Semple et al. |
| 6,214,798 B1 | 4/2001 | Semple et al. |
| 6,503,534 B1 | 1/2003 | Pellet et al. |
| 7,198,801 B2 | 4/2007 | Carrara et al. |
| 2004/0038903 A1 | 2/2004 | Luck et al. |
| 2004/0138610 A1 | 7/2004 | Cormier et al. |
| 2005/0042268 A1* | 2/2005 | Aschkenasy et al. ......... 424/448 |
| 2005/0245455 A1 | 11/2005 | Luck et al. |
| 2006/0135405 A1 | 6/2006 | Rischer et al. |
| 2008/0032935 A1 | 2/2008 | Engel et al. |
| 2009/0018085 A1 | 1/2009 | Luck et al. |
| 2009/0203622 A1 | 8/2009 | Persson |
| 2009/0209939 A1 | 8/2009 | Verespej et al. |
| 2010/0286603 A1 | 11/2010 | Winderstrom |
| 2010/0305042 A1 | 12/2010 | Olesen et al. |
| 2011/0039787 A1 | 2/2011 | Petri et al. |
| 2011/0053846 A1 | 3/2011 | Luck et al. |
| 2012/0046264 A1* | 2/2012 | Simes et al. ................. 514/180 |
| 2012/0172302 A1 | 7/2012 | Petri et al. |
| 2013/0018223 A1 | 1/2013 | Joseph |
| 2013/0029910 A1 | 1/2013 | Meulen et al. |
| 2013/0281661 A1 | 10/2013 | Rasmusse et al. |
| 2013/0281662 A1 | 10/2013 | Kalita et al. |
| 2013/0295166 A1 | 11/2013 | Grenier et al. |

FOREIGN PATENT DOCUMENTS

| | | |
|---|---|---|
| CN | 1411803 A | 4/2003 |
| EP | 0 002 749 B1 | 10/1983 |
| EP | 0 556 034 A1 | 8/1993 |
| EP | 1 003 774 B1 | 5/2000 |
| EP | 1 967 202 A1 | 9/2008 |
| FR | 2 776 520 A | 10/1999 |
| WO | WO 03/006049 A1 | 10/2003 |
| WO | WO 2004/080413 A2 | 9/2004 |
| WO | WO 2007/130809 A2 | 11/2007 |
| WO | WO 2008/135989 A1 | 11/2008 |
| WO | WO 2009/101533 A1 | 8/2009 |
| WO | WO 2011/004260 A2 | 1/2011 |

OTHER PUBLICATIONS

International Search Report issued on Apr. 19, 2012, in Application No. PCT/EP2012/050695.
Office Action (final) dated Oct. 8, 2013, U.S. Appl. No. 13/381,762.
Office Action dated Sep. 11, 2013, in U.S. Appl. No. 12/771,199.
Office Action dated Sep. 3, 2013, in U.S. Appl. No. 13/458,330.
The K-Zone, Biophysical data tables: standard man, Jul. 2004; printed Mar. 14, 2009 from www.kevinboone.com/biodat_stdman.html; 1 page.
"Alkaline Phosphatase," GP Notebook (Sep. 12, 2011), http://gpnotebook.co.uk/simplepage.cfm?ID=-1932525548.
Agerso, et al., "The dosing solution influence on the pharmacokinetic of degarelix, a new GnRHO antagonist, after s.c. administration to beagle dogs," European Journal of Pharmaceutical Sciences, vol. 20, pp. 335-340 (2003).
Albertsen et al., "Comparison of the Risk of Cardiovascular (CV) Events and Death in Patients Treated with Degarelix Compared with LHRH Agonists," J. Clin. Oncol., vol. 31 (2013).
Behn, et al., "The obesity epidemic and its cardiovascular consequences," Curr. Opin. Cardiol. vol. 21. pp. 353-360 (2006).
Berges, et al., "Effect of a new leuprorelin formulation on testosterone levels in patients with advanced prostate cancer," Cur. Med. Res. Opin., vol. 22, No. 4, pp. 649-655 (2006).

(Continued)

*Primary Examiner* — Lezah Roberts
*Assistant Examiner* — Nannette Holloman
(74) *Attorney, Agent, or Firm* — Finnegan, Henderson, Farabow, Garrett & Dunner LLP

(57) ABSTRACT

The subject invention provides improved testosterone gel formulations.

38 Claims, 11 Drawing Sheets

(56) References Cited

OTHER PUBLICATIONS

Boccon-Gibod, et al., "Cyproterone Acetate Lead-In Prevents Initial Rise of Serum Testosterone Induced by Luteinizing Hormone-Releasing Hormone Analogs in the Treatment of Metastatic Carcinoma of the Prostate," Eur. Urol.,vol. 12, pp. 400-402 (1986).
"Bone Specific Alkaline Phosphatase," The University of Iowa (UIHC), Department of Pathology, Laboratory Services Handbook, http://www.healthcare.uiowa.edu/path_handbook/handbook/test2238.html (Sep. 12, 2011).
Broqua et al., "Effects of the New GNRH Antagonist FE200486 one the Growth of the Adrogen-Dependent Prostate Tumor Dunning R-3327H," Gynecological Endocrinology, vol. 15, Supp. No. 1, p. 2, (Feb. 8 2001).
Broqua, et al., "Pharmacological Profile of a New, Potent, and Long-Acting Gonadotropin-Releasing Hormone Antagonist: Degarelix," JPET, vol. 301, pp. 95-102, (2002).
Cancer Trends Progress Report, http://progressreport.cancer.gov (Jun. 1, 2012).
Cetrotide package insert (Aug. 11, 2000).
Chernecky, et al., "Laboratory Tests and Diagnostic Procedures," Fifth Ed., WB Saunders & Company, Philadelphia (2008).
Co-pending U.S. Appl. No. 12/368,713.
Co-pending U.S. Appl. No. 12/368,935.
Co-pending U.S. Appl. No. 12/771,199.
Co-pending U.S. Appl. No. 12/774,113.
Co-pending U.S. Appl. No. 12/829,467.
Co-pending U.S. Appl. No. 12/901,270.
Co-pending U.S. Appl. No. 13/381,762.
Co-pending U.S. Appl. No. 13/458,330.
Co-pending U.S. Appl. No. 13/881,744.
Co-pending U.S. Appl. No. 13/881,751.
Co-pending U.S. Appl. No. 12/155,897.
Crawford et al., "A Phase III Extension Trial With a 1-Arm Crossover From Leuprolide to Degarelix: Comparison of Gonadotropin-Releasing Hormone Agonist and Antagonist Effect of Prostate Cancer," 186 The Journal of Urology 889-897 (2011).
de la Rosette et al., "Efficacy and safety of androgen deprivation therapy after switching from monthly leuprolide to monthly degarelix in patients with prostate cancer," International Journal of Clincal Practice, vol. 65(5), pp. 559-566 (2011).
Eastman et al., "Serum Alkaline Phosphatase: Normal Values by Sex and Age," Clinical Chemistry, vol. 23 (9), pp. 1769-1770 (1977).
Etzioni, et al., "Cancer Surveillance Series: Interpreting Trends in Prostate Cancer-Part III: Quantifying the Link Between Population Prostate-Specific Antigen Testing and Recent Declines in Prostate Cancer Mortality," J. Natl. Canc. Inst., vol. 91(12), pp. 1033-1039 (Jun. 16, 1999).
European Search Report & Opinion, EP Application No. 12168495.5 (Oct. 2, 2012).
FDA Consumer Safety Alert—Plenaxis (abarelix for injectable suspension); http://www.fda.gov/Drugs/ResourcesForYou/ucm078627.htm. (Aug. 24, 2009).
Etzioni, et al., "Cancer Surveillance Series: Interpreting Trends in Prostate Cancer-Part III: Quantifying the Link Between Population Prostate-Specific Antigen Testing and Recent Declines in Prostate Cancer Mortality," J. Natl. Canc. Inst., vol. 91(12), pp. 1033-1039 (Jun. 16. 1999).
FDA Consumer Safety Alert—Plenaxis (abarelix for injectable suspension); http://www.fda.gov/Drug/ResourcesForYou/ucm078627.htm. (Aug. 24, 2009).
FDA.GOV, Label for Degarelix for injection, Dec. 24, 2008, available at www.accessdata.fda.gov/drugsatfda_docs/label/2008/022201lbl.pdf, last visited Jun. 4. 2013.
Ferlay,et al., "Estimates of the cancer incidence and mortality in Europe in 2006," Annals of Oncology, vol. 18, pp. 581-592 (Feb. 7, 2007).
Fleming,et at, "Post-therapy changes in PSA as an outcome measure in prostate cancer clinical Trials," Nature Clinical Practice Oncoiology, vol. 3, No. 12, pp. 658-667 (Dec. 2006).

Forbes, et al., "FDA'S Adverse Drug Reaction Drug Dictionary and Its Role in Post-Marketing Surveillance," Drug Inf. J., vol. 20, pp. 135-145 (1986).
Gerlinger, et al., "Recommendation for Confidence interval and sample size calculation for the Pearl Index," The European Journal of Contraception and Reproductive Health Care, vol. 8. pp. 87-92 (2003).
Gillum, T., "The Merck Regulatory Dictionary: A Pragmatically Develop Drug Effects Vocabulary," Drug Info. J., vol. 23, pp. 217-220 (1989).
Gittelman et al., "A 1-Year, Open Label, Randomized Phase II Doe Finding Study of Degarelix for the Treatment of Prostate Cancer in North America," J. Urol., vol. 80, pp. 1986-1992 (Nov. 2008).
Granfors, et al., "Combined Orchiectomy and External Radiotherapy Versus Radiotherapy Alone for Nonmetastatic Prostate Cancer With or Without Pelvic Lymph Node Involvement: A Prospective Randomized Study," J. Urol., vol. 159, pp. 2030-2034 (Jun. 1998).
Hackman, et al., "Emerging Risk Factors for Atherosclerotic Vascular Disease," JAMA, vol. 290(7), pp. 932-940 (Aug. 20, 2003).
Hegele et al., "Biochemical Markers of Bone Turnover in Patients with Localized and Metastasized Prostate Cancer," Journal Compilation, vol. 99, pp. 330-334, (Sep. 7, 2006).
Hellerstedt, et al., "The Current State of Hormonal Therapy for Prostate Cancer," CA A Cancer J. Clin., vol. 52, pp. 154-179 (2002).
International Search Report in Application No. PCT/EP2012/050695 (Apr. 19, 2012).
International Search Report, in Application No. PCT/GB02/03116 (Sep. 12, 2002).
Iversen et al., "Improved outcomes with degarelix monotherapy compared with luteinizing hormone-releasing hormone (LHRH) agonists plus antiandrogen in the treatment of men with advanced prostate cancer", 29th Congress of the Scandinavian Association of Urologists, 2 pages (May 22, 2013).
Jiang at al., "Betidamino Acid-Scan of the GNRH Antagonist Acyline," J. Med. Chem., vol. 40, pp. 3739-3748 (1997).
Jiang, et al., "GnRH Antagonists: A New Generation of Long Acting Analogues Incorporating p-Ureido-phenylalanines at Positions 5 and 6," J. Med. Chem., vol. 44, pp. 453-467 (2001).
Kirk et al., "Immediate Versus deferred treatment for advanced prostatic cancer; initial results of the Medical Research Counsel trial," British Journal of Urology, vol. 79, pp. 235-246 (1997).
Lehmann, "Testing Statistical Hypotheses," Second Ed., John Wiley & Sons, New York (1986).
Lilja, et al., "Prostate-specific antigen and prostate cancer: prediction, detection and monitoring," Nature Reviews: Cancer: vol. 8, pp. 268-278 (Apr. 2008).
Lukka, et al., "Maximal androgen blockade for the treatment of metastatic prostate cancer—a systematic review" Current Oncology, vol. 13(3), pp. 81-93 (2006).
Lyseng-Williamson, "Degarelix: a guide to its use in advanced prostate cancer," Drugs Ther. Perspect., vol. 28(5), pp. 6-10 (2012).
Malkin, "Are techniques used for intramuscular injection based on research evidence?" Nursing Times, Dec. 16, 2008, http://www.nursingtimes.net/nursing-practice/clinical-zones/prescribing/are-techniques-used-for-intramuscular-injection-based-on-research-evidence/1952004.article.
McNeil, et al., "On the Elicitation of Preferences for Alternative Therapies," New Engl. J. Med , vol. 306(21) No. 21, pp. 1259-1262 (May 27, 1982).
Messing, et al., "Immediate Hormonal Therapy Compared with Observation after Radical Prostatectomy and Pelvic Lymphadenectomy in Men with Node-Positive Prostate Cancer," New Eng. J. Med., vol. 341, pp. 1781-1788 (Dec. 9, 1999).
Miller et al., "Disease control-related outcomes from an analysis of six comparative randomised clinical trials of degarelix versus luteinising hormone-releasing hormone (LHRH) agonists," (2013).
Mongiat-Artus, et al., "Abarelix: the first gonadotrophin-releasing hormone antagonist for the treatment of prostate cancer," Expert Opin. Pharmacother, vol. 5(10), pp. 2171-2179 (2004).
Office Action dated Jul. 25, 2013, U.S. Appl. No. 12/829,467.
Office Action dated Jul. 26, 2013, U.S. Appl. No. 12/901,270.
Office Action dated Jun. 11, 2013, U.S. Appl. No. 13/381,762.
Office Action dated Jun. 6, 2013, U.S. Appl. No. 12/774,113.

(56) References Cited

OTHER PUBLICATIONS

Office Action mailed Apr. 2, 2012, in copending U.S. Appl. No. 12/368,935.
Office Action mailed Jan. 31, 2013, in copending U.S. Appl. No. 12/901,270.
Office Action mailed Mar. 1, 2011, in copending U.S. Appl. No. 12/368,713.
Office Action mailed Mar. 8, 2011, in copending U.S. Appl. No. 12/155,897.
Office Action mailed Oct. 12, 2011, in U.S. Appl. No. 12/155,897.
Office Action mailed Oct. 22, 2009, in co-pending U.S. Appl. No. 12/155,897.
People's Republic of China First Office Action in corresponding Application No. 201080019696.2, 2 pages (Feb. 25, 2013).
Persad, "Leuprorelin Acetate in Prostate Cancer: A European Update," IJCP, vol. 56(5), pp. 389-396 (2002).
Romero-Corral, et al., "Association of bodyweight with total mortality and with cardiovascular events in coronary artery disease: a systematic review of cohort studies," Lancet, vol. 368, pp. 666-678 (Aug. 19, 2006).
Saltzman, A., "Adverse Reaction Terminology Standardization: A Report on Schering-Plough's Use of the WHO Dictionary and the Formation of the WHO Adverse Reaction Terminology Users Group (WUG) Consortium," Drug Info. J., vol. 19, pp. 35-41 (1985).
Smith et al., "Cardiovascular Safety of Degarelix: Results From a 12-Month, Comparative, Randomized, Open Label, Parallel Group Phase III Trial in Patients With Prostate Cancer," J. Urol., vol. 184, pp. 2313-2319 (Dec. 2010).
Smith, M.R. et al., "Gonadotropin-Releasing Hormone Blockers and Cardiovascular Disease Risk: Analysis of Prospective Clinical Trials of Degarelix," J. Urol., vol. 186(5), No. 1835-1842 (Nov. 2011).
Sorbera et al., "Degarelix Acetate", Drugs of the Future, vol. 31(9), pp. 755-766 (2006).
Spilker, Bert, "Guide to Clinical Trials," Raven Press; Ltd., New York (1991).
Spilker, Bert, "Quality of Life and Pharmacoeconomics in Clinical Trials," Second E., Lippincott—Raven Publishers, New York (1996).
Steinberg, et al.; "Degarelix: A Gonadotropin-Releasing Hormone Antagonist for the Management of Prostate Cancer," Clinical Therapeutics, vol. 31, pp. 2312-2331, (2009).
Stephens, M.D.B., "The Detection of New Adverse Drug Reactions," Stockton Press, New York (1988).
Teal, et al. "Adverse Drug Experience Management: A Brief Review of the McNeil Pharmaceutical System," Drug Info. J., vol. 19, pp, 17-25 (1985).
Thompson, et al., "Sudden Death to Disease Flare With Luteinizing Hormone-Releasing Hormone Agonist Therapy for Carcinoma of the Prostate," J. Urol., vol. 144, pp. 1479-1480 (Dec. 1990).
Turner, et al., "The Processing of Adverse Reaction Reports at FDA," Drug. Inf. J., vol. 20, pp. 147-150 (1986).
Van Poppel et al., "A One-Year, Multicentre, Randomised Study of Degarelix a Gonadatrophi-Releasing Hormone (GNRH) Receptor Blocker, in Prostate Cancer Patients," Eur. Urol. Suppl. vol. 5(2). p. 251 (2005).
Van Poppel, "Evaluation of degareilx in the management of prostate cancer," Cancer Management and Research, vol. 2, pp. 39-52 (2010).
Wiegel et al., "Neoadjuvant Androgen Deprivation Therapy for Prostate Volume Reduction, Lower Urinary Tract Symptom Relief and Quality of Life Improvement in Men with Intermediate- to High-risk Prostate Cancer: A Randomised Non-inferiority Trial of Degarelix versus Goserelin plus Bicalutamide," Clin. Oncol., vol. 25, No. 3, pp. 190-196 (Mar. 2013).
Wilson, et al., "Leuprolide acetate: a drug of diverse clinical applications," Expert Opin. Investig. Drugs, vol. 16, pp. 1851-1863 (2007).
Wilson, et al., "Prediction of Coronary Heart Disease Using Risk Factor Categories," Circulation, vol. 97, pp. 1837-1847 (1998).
Yannuci, et al., "The Effect of Androgen Deprivation Therapy on Fasting Serum Lipid and Glucose Parameters," J. Urol., vol. 176, pp. 520-525 (Aug. 2006).

\* cited by examiner

TESTOSTERONE FORMULATIONS

This is a national stage entry application of International Patent Application No. PCT/EP2012/050695, filed Jan. 18, 2012, which claims the benefit of priority of European Patent Application No. 11152210.8, filed Jan. 26, 2011, and U.S. Provisional Application No. 61/436,207, filed Jan. 26, 2011, all of which are incorporated herein by reference in their entireties.

FIELD OF THE INVENTION

The subject invention lies in the field of transdermal testosterone formulations.

BACKGROUND OF THE INVENTION

Systemic delivery of active agents across the skin or mucosal membrane is convenient, pain-free, non-invasive and circumvents problems associated with the "first pass effect". Such transdermal drug delivery is typically restricted to low-molecular weight drugs and drugs with specific lipophilic/hydrophilic balance able to penetrate the stratum corneum.

Transdermal drug delivery systems enable chemical modification of the barrier properties of skin to effectively and efficiently permit penetration thereof. Known drawbacks of transdermal delivery systems are, for example, the length of time needed for penetration, frequent dosing regimen, and the volume size of a transdermal composition needed to transdermally deliver a sufficient therapeutic amount of the active agent. Due to e.g. the need for such a large dose volume, the composition applied transdermally is inevitably maintained on the treated skin area for a long period of time, thereby exposing the active agent to be transdermally delivered to degradation processes and also exposing the immediate surroundings (e.g. clothing, spouses etc.) of the subject treated to the active agent.

Testosterone is an androgen, anabolic steroid which is primarily secreted in the testes of males and the ovaries of females, and in much smaller amounts by the adrenal glands. In men, testosterone plays a key role in the development of male reproductive tissues such as the testis and prostate, as well as promotes secondary sexual characteristics such as increased muscle, bone mass and hair growth. In women, testosterone plays a role in the development of pubic and axillary hair, sexual libido, bone density, muscle tone, and vitality. Testosterone is essential for health and well-being as well as the prevention of osteoporosis in both males and females.

Examples of known transdermal testosterone formulations for the treatment of e.g. hypogonadism are FORTESTA® (TOSTRAN®/TOSTREX®/ITNOGEN®) (ProStrakan Group plc), a 2% testosterone gel containing ethanol, propanol, propylene glycol, carbomer, triethanolamine, purified water, butylhydroxytoluene and oleic acid, TESTIM® (Auxilium Pharmaceuticals), a 1% testosterone gel containing pentadecalactone, acrylate, carbomer, glycerin, polyethylene glycol (PEG), propylene glycol, ethanol, tromethamine and water, and ANDROGEL® (TESTOGEL®) a 1% testosterone gel containing ethanol, isopropyl myristate, carbomer, sodium hydroxide and water.

U.S. Pat. No. 7,198,801 discloses formulations for transdermal or transmucosal administration of active agents, such as testosterone, containing an alkanol, a polyalcohol, and a monoalkyl ether of diethylene glycol. The formulations disclosed in U.S. Pat. No. 7,198,801 are reported to be substantially odor- and irritation-free as a result of the absence of long chain fatty alcohols, long-chain fatty acids, and long-chain fatty esters in the formulations.

As any product of technology at all times, also the latter formulations are not free of their own drawbacks and can further be improved upon. There is still a need for a transdermal formulation that delivers therapeutically effective amounts of testosterone in a controlled manner to subjects in need thereof, such formulation having high skin tolerability, efficient and regulated skin absorption, enabling daily doses having lower volumes and thus shorter administration regimens.

SUMMARY OF THE INVENTION

The present invention provides a transdermal or transmucosal formulation comprising:
2% wt of testosterone, and
a penetration enhancing system comprising: $C_2$ to $C_4$ alkanol, polyalcohol, and monoalkyl ether of diethylene glycol,
wherein said formulation is substantially free of long-chain fatty alcohols, long-chain fatty acids, and long-chain fatty esters.

The formulations of the invention provide controlled plasma levels of testosterone and further enable a lower administration volume and thus shorter administration regimens of treatment. Such controlled plasma levels achieved with a formulation of the invention provide regulated transdermal or transmucosal delivery of testosterone to a subject wherein plasmatic peaks of testosterone are reduced or minimized, thereby avoiding the drawbacks and side effects of known formulations.

In one aspect the invention provides a transdermal or transmucosal formulation comprising: 2% wt of testosterone, $C_2$ to $C_4$ alkanol, polyalcohol, and monoalkyl ether of diethylene glycol, wherein said formulation is substantially free of long-chain fatty alcohols, long-chain fatty acids, and long-chain fatty esters.

In another aspect the invention provides a transdermal or transmucosal formulation comprising: 2% wt of testosterone, 44.0% wt of ethanol, 20.0% wt of propylene glycol, and 5.0% wt of diethylene glycol monoethyl ether, wherein said formulation is substantially free of long-chain fatty alcohols, long-chain fatty acids, and long-chain fatty esters.

In a further aspect the invention provides a transdermal or transmucosal formulation comprising: 2% wt of testosterone, 44.0% wt of ethanol, 20.0% wt of propylene glycol, 5.0% wt of diethylene glycol monoethyl ether, 1.20% wt carbomer, 0.35% wt triethanolamine, 0.06% wt edetate disodium and water (q.s.) wherein said formulation is substantially free of long-chain fatty alcohols, long-chain fatty acids, and long-chain fatty esters.

In a further aspect the invention provides a transde inal or transmucosal formulation consisting of 2% wt of testosterone, 44.0% wt of ethanol, 20.0% wt of propylene glycol, 5.0% wt of diethylene glycol monoethyl ether, 1.20% wt carbomer, 0.35% wt triethanolamine, 0.06% wt edetate disodium and water (q.s.).

Furthermore, the present invention relates to a method for administering testosterone to a mammal in need thereof, said method comprises transdermally administering to a skin or mucosal membrane of said mammal a formulation of the invention.

The invention further relates to a method of treating a disease or disorder associated with reduced endogenous testosterone production, said method comprises transdermally administering to a skin or mucosal membrane of a mammal a formulation of the invention.

In another one of its aspects the invention provides a method of treating a disease or disorder associated with reduced endogenous testosterone production in a male subject, said method comprising transdermally administering to a skin or mucosal membrane of a male subject a formulation comprising: 1-2% wt of testosterone, $C_2$ to $C_4$ alkanol, 20.0% wt of propylene glycol, and monoalkyl ether of diethylene glycol, wherein said formulation is substantially free of long-chain fatty alcohols, long-chain fatty acids, and long-chain fatty esters.

In another one of its aspects the invention provides a method of treating a disease or disorder associated with reduced endogenous testosterone production in a male subject, said method comprises transdermally administering to a skin or mucosal membrane of a male subject a formulation comprising: 1-2% wt of testosterone, $C_2$ to $C_4$ alkanol, 20.0% wt of propylene glycol, monoalkyl ether of diethylene glycol, gelling agent, neutralizing agent, chelating agent, and solvent, wherein said formulation is substantially free of long-chain fatty alcohols, long-chain fatty acids, and long-chain fatty esters.

In another one of its aspects the invention provides a method of treating a disease or disorder associated with reduced endogenous testosterone production in a male subject, said method comprising transdermally administering to a skin or mucosal membrane of a male subject a formulation comprising 1-2% wt of testosterone, 44% wt ethanol, 20.0% wt of propylene glycol, 5%/wt of monoethyl ether of diethylene glycol, 1.2% wt carbomer, 0.35% wt triethanolamine, 0.06% wt edetate disodium and water (q.s.) wherein said formulation is substantially free of long-chain fatty alcohols, long-chain fatty acids, and long-chain fatty esters.

In another one of its aspects the invention provides a method of treating a disease or disorder associated with reduced endogenous testosterone production in a male subject, said method comprising transdermally administering to a skin or mucosal membrane of a male subject a formulation consisting of 1-2% wt of testosterone, 44% wt ethanol, 20.0% wt of propylene glycol, 5% wt monoethyl ether of diethylene glycol, 1.2% wt carbomer, 0.35% wt triethanolamine, 0.06% wt edetate disodium and water.

In another aspect the invention provides a transdermal or transmucosal formulation of the invention for use in the treatment of a disease or disorder associated with reduced endogenous testosterone production.

The formulations of the invention were shown to provide controlled testosterone plasma levels. The formulations of the invention further demonstrated favorable once daily administration volumes as a result of which the administration time was beneficially shortened, the amount of unabsorbed testosterone left on the skin of a subject was minimized, the exposure of the surroundings to the testosterone was minimized and the exposure of the testosterone to degradation processes was minimized. Accordingly, formulations of the invention were shown to deliver therapeutic amounts of testosterone by a convenient, clinically effective, user-friendly and simplified dosing regimen.

BRIEF DESCRIPTION OF THE DRAWINGS

In order to understand the invention and to see how it may be carried out in practice, embodiments will now be described, by way of non-limiting example only, with reference to the accompanying drawings, in which.

DETAILED DESCRIPTION OF EMBODIMENTS

Figure 1:
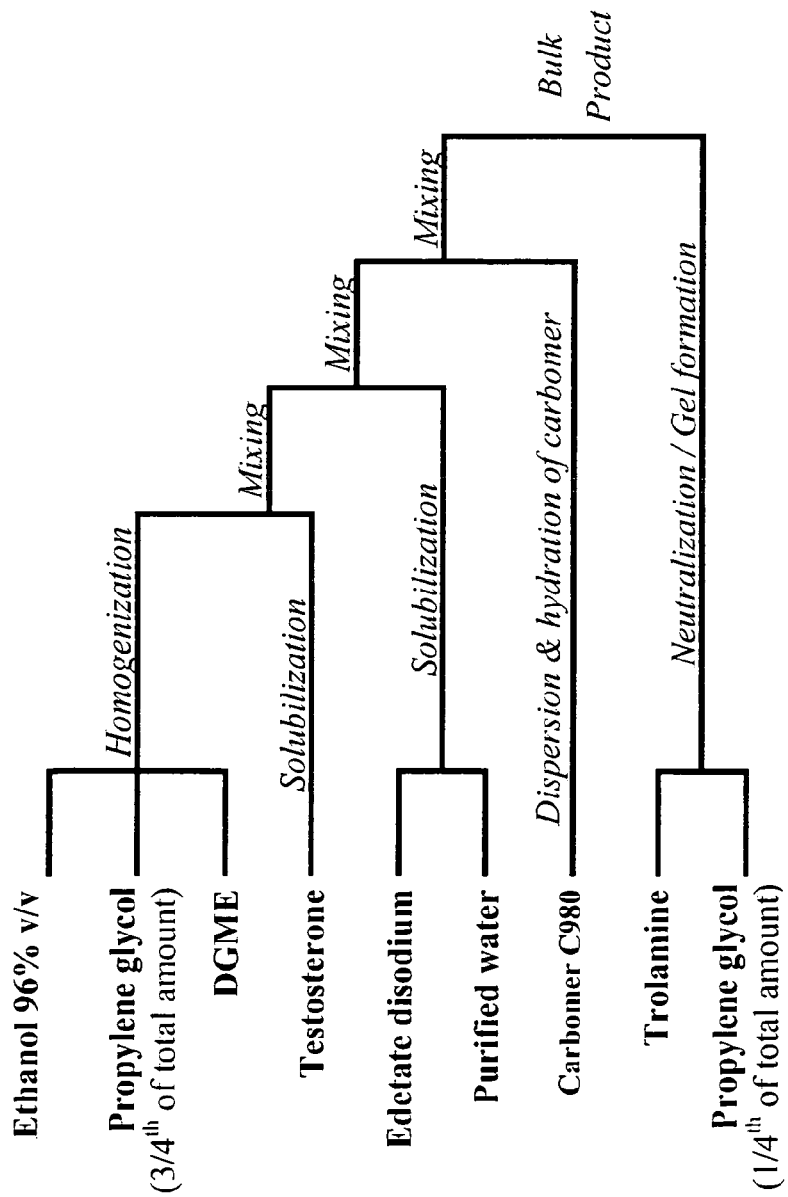
FIG. 1 shows a flow chart of the preparation of a testosterone gel formulation of the invention.

In one of its aspects the invention provides a transdermal or transmucosal formulation comprising 2% wt of testosterone and a penetration enhancing system comprising $C_2$ to $C_4$ alkanol, polyalcohol and monoalkyl ether of diethylene glycol, wherein said formulation is substantially free of long-chain fatty alcohols, long-chain fatty acids, and long-chain fatty esters.

It should be noted that the selection of the types and amounts of the components present in a formulation of the invention, other than testosterone, were based on several factors, including, among others: potential for skin permeation of testosterone from a formulation of the invention, ease of manufacturing, compatibility between the various components of a formulation of the invention, and stability of a formulation of the invention. It is furthermore noted that the components of the permeation enhancing system as defined herein are present in an amount sufficient to provide permeation enhancement of testosterone through dermal or mucosal surfaces.

Unless expressly specified otherwise, the term "comprising" is used in the context of the present application to indicate that further members may optionally be present in addition to the members explicitly mentioned. It is, however, contemplated as a specific embodiment of the present invention that the term "comprising" encompasses the possibility of no further members being present. In other words, for the purpose of this embodiment, "comprising" is to be understood as having the meaning of "consisting of".

The following detailed description discloses specific and/or preferred variants of the individual features of the invention. The present invention also contemplates as particularly preferred embodiments those embodiments, which are generated by combining two or more of the specific and/or preferred variants described for two or more of the features of the present invention.

Unless expressly specified otherwise, all indications of relative amounts in the present application are made on a weight/weight basis. Indications of relative amounts of a component characterized by a generic term are intended to refer to the total amount of all specific variants or members covered by said generic term. If a certain component defined by a generic term is specified to be present in a certain relative amount, and if this component is further characterized to be a specific variant or member covered by the generic term, it is intended that no other variants or members covered by the generic term are additionally present such that the total relative amount of components covered by the generic term exceeds the specified relative amount, more preferably, in such case, no other variants or members covered by the generic term are present at all.

When referring to a formulation comprising "2% wt testosterone", such formulation should be understood to allow for a pharmaceutically acceptable variation in the % wt of testosterone. In the context of this invention, a pharmaceutically acceptable variation ranges from 1.9% wt testosterone to 2.1% wt testosterone.

The terms "transdermal formulation" or "transmucosal formulation" should be understood to encompass a formulation of the invention capable of delivering testosterone to a mammal administered with said formulation, by permeating the testosterone through the skin or mucosal tissue (or membrane), said formulation being topically applied and entering into the bloodstream of said mammal.

"Transdermal delivery" as used herein should be understood to encompass transdermal, percutaneous and transmucosal administration, i.e. delivery by passage/permeation of a drug through the skin or mucosal tissue into the bloodstream.

The term "skin" or "skin tissue" or "skin membrane" as used herein interchangeably should be understood to encompass any dermal membrane (including any epidermis or dermis layer of a skin membrane), including any hairy or glabrous cutaneous membrane.

The term "mucosa" or "mucosal tissue" or "mucosal membrane" as used herein interchangeably should be understood to encompass any moist anatomical membrane or surface on a mammal that can be permeated without swallowing such as oral, buccal, auricular, vaginal, rectal, nasal or ophthalmic surfaces.

The term "topical" or "topically" is used herein as referring to direct contact of a formulation of the invention, with a surface area on a mammal including any portion of a skin membrane or mucosal membrane.

The term "mammal" as used herein should be understood to encompass any mammal. In one embodiment, the mammal is a human mammal. In another embodiment, the mammal is a male human. In yet another embodiment, the mammal is a female human.

When referring to testosterone, it should be understood to refer to the androgen steroidal hormone 17-β-hydroxyandrostenone also named (8R, 9S, 10R, 13S, 14S, 17S)-17-hydroxy-10,13-dimethyl-1,2,6,7,8,9,11,12,14,15,16,17dodecahydrocyclopenta[a]phenanthren-3-one (CAS Registry Number 58-22-0).

Examples of other androgens which may be used in a transdermal or transmucosal formulation of the invention include, but are not limited to, any esters of testosterone (such as testosterone enanthate, propionate, cypionate, phenylacetate, acetate, isobutyrate, buciclate, heptanoate, decanoate, undecanoate, caprate and isocaprate esters), 4-dihydrotestosterone, and any pharmaceutically acceptable derivatives of testosterone such as for example methyl testosterone, testolactone, oxymetholone and fluoxymesterone. These androgens may be used singly or in combinations of two or more thereof.

As noted hereinabove, a formulation of the invention is substantially free of long-chain fatty alcohols, long-chain fatty acids, and long-chain fatty esters. Such an omission of long chain fatty alcohols, long-chain fatty acids, and long-chain fatty esters provides a formulation that does not have an unpleasant odor, irritation, and/or greasy texture caused by formulations that include one or more of such compounds, resulting in greater patient compliance.

"Long-chain fatty alcohols, long-chain fatty acids, and long-chain fatty esters" as used herein should be understood to encompass fatty alcohols and fatty acids having a branched or linear carbon body having 8 or more carbon atoms, and esters thereof, i.e. fatty esters having a branched or linear acid moiety having 8 or more carbon atoms or having a branched or linear alcohol moiety having 8 or more carbon atoms.

"substantially free of long-chain fatty alcohols, long-chain fatty acids, and long-chain fatty esters" as used herein should be understood to mean comprising fatty alcohols, fatty acids and/or fatty esters in a total amount of less than about 0.1% wt.

The invention thus provides a transdermal or transmucosal formulation comprising 2% wt of testosterone, $C_2$ to $C_4$ alkanol, polyalcohol and monoalkyl ether of diethylene glycol, wherein said formulation is substantially free of long-chain fatty alcohols, long-chain fatty acids, and long-chain fatty esters.

In one embodiment a transdermal or transmucosal formulation of the invention further comprises at least one of a gelling agent, a neutralizing agent, a chelating agent and a solvent or any combinations thereof.

For example, in one embodiment a transdermal or transmucosal formulation of the invention comprises 2% wt of testosterone, $C_2$ to $C_4$ alkanol, polyalcohol, monoalkyl ether of diethylene glycol and gelling agent. In another embodiment a transdermal or transmucosal formulation of the invention comprises 2% wt of testosterone, $C_2$ to $C_4$ alkanol, polyalcohol, monoalkyl ether of diethylene glycol, gelling agent and neutralizing agent. In a further embodiment a transdermal or transmucosal formulation of the invention comprises 2% wt of testosterone, $C_2$ to $C_4$ alkanol, polyalcohol, monoalkyl ether of diethylene glycol, gelling agent, neutralizing agent and chelating agent. In yet another embodiment a transdermal or transmucosal formulation of the invention comprises 2% wt of testosterone, $C_2$ to $C_4$ alkanol, polyalcohol, monoalkyl ether of diethylene glycol, gelling agent, neutralizing agent, chelating agent and solvent.

It is envisaged that a formulation of the invention comprises $C_2$-$C_4$ alkanol in an amount between about 5-50% wt (e.g. about 5, 10, 15, 20, 25, 30, 35, 40, 45, 50% wt), polyalcohol in an amount between about 1-30% wt (e.g. about 1, 2, 3, 4, 5, 10, 15, 20, 25, 30% wt), monoalkyl ether of diethylene glycol in an amount of between about 0.2-25% wt (e.g. about 0.2, 0.3, 0.4, 0.5, 0.6, 0.7, 0.8, 0.9, 1.0, 2.0, 3.0, 4.0, 5.0, 6.0, 7.0, 8.0, 9.0, 10.0, 15, 20, 25% wt), gelling agent in an amount between about 0.05-4% wt (e.g. about 0.05, 0.06, 0.07, 0.08, 0.09, 0.1, 0.2, 0.3, 0.4, 0.5, 0.6, 0.7, 0.8, 0.9, 1, 1.5, 2, 2.5, 3, 3.5, 4% wt), neutralizing agent in an amount between about 0.05-1% wt (e.g. about 0.05, 0.06, 0.07, 0.08, 0.09, 0.1, 0.2, 0.3, 0.4, 0.5, 0.6, 0.7, 0.8, 0.9, 1% wt) and chelating agent in an amount between about 0.001-5.0% wt (e.g. about 0.001, 0.002, 0.003, 0.004, 0.005, 0.006, 0.007, 0.008, 0.009, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0, 1.5, 2.0, 2.5, 3.0, 3.5, 4, 4.5, 5.0% wt).

A "penetration enhancing system" as used herein should be understood to comprise $C_2$ to $C_4$ alkanol, polyalcohol and monoalkyl ether of diethylene glycol, which together qualitatively and/or quantitatively enhance the absorption and/or penetration of testosterone of a formulation of the invention through a skin or mucosal membrane of a mammal administered with said formulation (as compared with the transdermal delivery of testosterone without said penetration enhancing system).

The term "$C_2$ to $C_4$ alkanol" as used herein should be understood to encompass one or more $C_2$ to $C_4$ alkanes substituted with a hydroxy group (—OH).

In one embodiment, an alkanol utilized by a formulation of the invention is one or more selected from the group consisting of ethanol, isopropanol and n-propanol. In another embodiment said alkanol is ethanol. In a further embodiment, said alkanol is ethanol present in an amount of about 44.0% wt in a formulation of the invention.

In some embodiments an alkanol is also utilized by a formulation of the invention (such as for example ethanol) as the primary solvent for the testosterone in a formulation of the invention. The quantity of the alkanol should be sufficient to at least fully solubilise the testosterone. Additionally, alkanols, such as ethanol, are known to be efficient skin permeation enhancers which act by extracting polar stratum corneum lipids and, consequently, increase partitioning for numerous drug substances. However, as demonstrated herein below (see example 1), the inventors of the present invention found that in order to enhance the penetration of a formulation of the invention, said alkanol (e.g. ethanol) may be present in a formulation of the invention in amounts of up to 50% wt, and in a particular embodiment in an amount of up to 44% wt.

In some embodiments, a formulation of the invention comprises alkanol in a hydroalcoholic mixture with water.

In the context of the present invention, the term "polyalcohol" as used herein should be understood to encompass one or more of a $C_2$ to $C_6$ alkane or $C_2$ to $C_6$ alkene, substituted with two or more hydroxy groups.

In some embodiments, a polyalcohol comprised in a formulation of the invention is one or more selected from the group consisting of ethylene glycol, propylene glycol, butylene glycol, and hexylene glycol. In one embodiment a polyalcohol comprised in a formulation of the invention is propylene glycol. In another embodiment a formulation of the invention comprises propylene glycol in an amount of about 20.0% wt.

The term "monoalkyl ether of diethylene glycol" as used herein should be understood to encompass one or more diethylene glycols substituted with a $C_1$ to $C_6$ alkyl ether.

In one embodiment, monoalkyl ether of diethylene glycol comprised in a formulation of the invention is one or both of diethylene glycol monoethyl ether (DGME) and diethylene glycol monomethyl ether. In another embodiment, a formulation of the invention comprises diethylene glycol monoethyl ether. In yet another embodiment, a formulation of the invention comprises diethylene glycol monoethyl ether in an amount of about 5.0% wt.

The term "gelling agent" as used herein should be understood to encompass any agent capable of altering the viscosity of a formulation. A gelling agent used in a formulation of the invention can be one or more selected from the group including: carbomer, carboxyethylene or polyacrylic acid such as carbomer or carbopol 980NF (CARBOPOL™ 980 NF) or 940 NF, 981 or 941 NF, 1382 or 1342 NF, 5984 or 934 NF, ETD 2020, 2050, 934P NF, 971P NF, 974P NF, Ultrez 10 NF, Pemulen TR-1 NF or TR-2 NF and Noveon AA-1 USP, cellulose derivatives such as ethylcellulose (EC), hydroxypropylmethylcellulose (HPMC), ethylhydroxyethylcellulose (EHEC), carboxymethylcellulose (CMC), hydroxypropylcellulose (HPC) (Klucel different grades), hydroxyethylcellulose (HEC) (Natrosol grades), HPMCP 55, and Methocel grades, natural gums such as arabic, xanthan, guar gums, and alginates, polyvinylpyrrolidone derivatives such as Kollidon grades, polyoxyethylene-polyoxypropylene copolymers such as Lutrol F grades 68 and 127, chitosan, polyvinyl alcohols, pectins, and veegum grades. A tertiary amine, such as triethanolamine or trolamine, can be included to thicken and neutralize the system.

In one embodiment, the gelling agent comprised in a formulation of the invention is a carbomer. Carbomer relates to a class of homopolymers of acrylic acid with a high molecular weight, which are cross-linked with any of several polyalcohol allyl ethers. Non-limiting examples of carbomers are carbomer 940, carbomer 973, carbomer 980NF, and carbomer C981 NF (wherein the digit indicates the average molecular weight of the polymer chains). In a particular embodiment, the gelling agent comprised in a formulation of the invention is carbomer C980NF. In yet another embodiment, the gelling agent comprised in a formulation of the invention is carbomer C980NF in an amount of 1.20% wt.

The term "neutralizing agent" as used herein should be understood to encompass one or more agents capable of neutralizing an acidic or basic component of a formulation of the invention in order to achieve a stable and homogeneous formulation. Non-limiting examples of a neutralizing agent include: diethylamine, diisopropylamine, a ternary amine such as triethanolamine or tromethamine, tetrahydroxypropylethylendiamine, and alkalis such as KOH or NaOH solution. For example, neutralization of hydro-alcoholic gels containing carbomer polymer can be accomplished using different bases. The salt of the carbomer polymer must be swellable in the solvent system, otherwise it will precipitate and no thickening effect will occur. Triethanolamine can be used in hydro-alcoholic gels with up to 50% alcohol.

In one embodiment, a neutralizing agent comprised in a formulation of the invention is triethanolamine (also named trolamine interchangeably). In another embodiment, a neutralizing agent comprised in a formulation of the invention is triethanolamine in an amount of about 0.35% wt. This concentration of triethanolamine (0.35% wt) in a formulation of the invention provides a pH level of between about 5.6 to about 6.8.

The term "chelating agent" as used herein should be understood to encompass one or more agents which complex and segregate residual traces of free multivalent cations susceptible to cause the physical degradation of the gel matrix (thereby causing loss of viscosity and breakdown of the formulation). Chelating agents provide improved physical stability and robustness of a formulation of the invention.

In one embodiment, a chelating agent comprised in a formulation of the invention is edetate disodium. In further embodiments, a chelating agent comprised in a formulation of the invention is edetate disodium in an amount of about 0.06% wt.

As used herein the term "solvent" may encompass any type of solvent suitable for use in a transdermal or transmucosal formulation of the invention, and may be the same or different than any other component of a formulation of the invention, as detailed herein above.

In one embodiment, a solvent comprised in a formulation of the invention is water.

The invention further provides a transdermal or transmucosal formulation comprising: 2% wt of testosterone, 44.0% wt of ethanol, 20.0% wt of propylene glycol, and 5.0% wt of diethylene glycol monoethyl ether, wherein said formulation is substantially free of long-chain fatty alcohols, long-chain fatty acids, and long-chain fatty esters.

The subject invention specifically provides a transdermal or transmucosal formulation comprising: 2% wt of testosterone, 44.0% wt of ethanol, 20.0% wt of propylene glycol, 5.0% wt of diethylene glycol monoethyl ether, 1.20% wt of carbomer, 0.35% wt of triethanolamine, 0.06% wt of edetate disodium and water (q.s.) wherein said formulation is substantially free of long-chain fatty alcohols, long-chain fatty acids, and long-chain fatty esters.

The subject invention further provides a transdermal or transmucosal formulation consisting of 2% wt of testosterone, 44.0% wt of ethanol, 20.0% wt of propylene glycol, 5.0% wt of diethylene glycol monoethyl ether, 1.20% wt of carbomer, 0.35% wt of triethanolamine, 0.06% wt of edetate disodium and water (q.s.).

In a specific embodiment, the carbomer is carbomer C980 NF. In another specific embodiment carbomer C980NF is present in an amount of 1.20% wt in a formulation of the invention.

The subject invention thus provides an advanced transdermal permeation enhancing system, comprising a combination of volatile solvent (e.g. ethanol) and non-volatile cosolvents (e.g. propylene glycol and e.g. diethylene glycol monoethyl ether), embedded in an aqueous gel matrix of acrylic polymer.

In some embodiments a formulation of the invention further comprises at least one of a buffering agent, moisturizing agent, humectant, surfactant, antioxidant, emollient, or buffer.

In some other embodiments, a formulation of the invention is in the form of a gel, lotion, cream, spray, aerosol, ointment, emulsion, suspension, liposomal system, lacquer, patch, bandage, buccal tablet, wafer, sublingual tablet, suppository, vaginal dosage form or occlusive dressing. In a particular embodiment, the formulation is a gel.

In other embodiments, a formulation of the invention is in the form of at least one of the following: a clear (invisible) formulation, a water washable formulation, a cool-to-the-touch formulation, a quick-drying formulation, a spreadable formulation and a non-greasy formulation.

In some embodiments said formulation is in the form of a gel. In other embodiments, said formulation is in the form of a clear invisible gel.

In some embodiments, a formulation of the present invention is applied directly to the skin by, for example a gel, an ointment, or a cream or indirectly through a patch, bandage, or other occlusive dressing.

A transdermal formulation of the invention may be topically applied to any body part, such as to the chest, thigh, abdomen, shoulder, upper arm, upper torso, back, neck, feet, hands, axilla, or scrotum. In one embodiment, a formulation of the invention is applied to the abdomen. In another embodiment, a formulation of the invention is applied to the abdomen once a day. In another embodiment, a formulation of the invention is applied to the upper arm. In another embodiment, a formulation of the invention is applied to the upper arm once a day.

In one embodiment, a formulation in the form of a gel is applied to an area of skin of from about 100 $cm^2$ up to about 1500 $cm^2$, so that testosterone is applied e.g. at about 50 micrograms per square centimeter of skin. Application may be to alternate areas of the body as applications alternate. This may be advantageous in alleviating any sensitivity of the skin to repeated exposure to components of the formulation.

A formulation of the invention may be applied once daily, or multiple times per day depending upon the condition of the patient.

In some embodiments, a formulation of the invention is adapted for transdermal or transmucosal administration according to a schedule (dosing regimen) having a periodicity selected from once to five times daily dosing, once-weekly dosing or bi-weekly dosing.

In some embodiments, said formulation is adapted for a once daily transdermal or transmucosal administration. In other embodiments, said formulation is adapted for a once daily transdermal or transmucosal administration to the abdomen (or a portion thereof) of a mammal in need thereof. In yet other embodiments, said formulation is adapted for a once daily transdermal or transmucosal administration to the upper arm (or a portion thereof) of a mammal in need thereof.

The present invention further provides a method for administering testosterone to a mammal in need thereof which comprises transdermally administering to a skin or mucosal membrane of a mammal a formulation of the invention. It is envisaged that the administration is for the treatment of diseases and disorders associated with reduced endogenous testosterone production.

In another aspect the invention provides a method of treating a disease or disorder associated with reduced endogenous testosterone production, said method comprises transdermally administering to a skin or mucosal membrane of a mammal a formulation of the invention.

In another one of its aspects the invention provides a method of treating a disease or disorder associated with reduced endogenous testosterone production in a male subject, said method comprising transdermally administering to a skin or mucosal membrane of a male subject a formulation comprising: 1-2% wt of testosterone, $C_2$ to $C_4$ alkanol, 20.0% wt of propylene glycol, and monoalkyl ether of diethylene glycol, wherein said formulation is substantially free of long-chain fatty alcohols, long-chain fatty acids, and long-chain fatty esters.

In a further aspect the invention provides a method of treating a disease or disorder associated with reduced endogenous testosterone production in a male subject, said method comprises transdermally administering to a skin or mucosal membrane of a male subject a formulation comprising: 1-2% wt of testosterone, $C_2$ to $C_4$ alkanol, 20.0% wt of propylene glycol, monoalkyl ether of diethylene glycol, gelling agent, neutralizing agent, chelating agent and solvent wherein said formulation is substantially free of long-chain fatty alcohols, long-chain fatty acids, and long-chain fatty esters.

In a specific embodiment, the invention provides method of treating a disease or disorder associated with reduced endogenous testosterone production in a male subject, said method comprising transdermally administering to a skin or mucosal membrane of a male subject a formulation comprising 1-2% wt of testosterone, 44% wt ethanol, 20.0% wt of propylene glycol, 5% wt of monoethyl ether of diethylene glycol, 1.2% wt of carbomer, 0.35% wt of triethanolamine, 0.06% wt of edetate disodium and water (q.s.) wherein said formulation is substantially free of long-chain fatty alcohols, long-chain fatty acids, and long-chain fatty esters.

In a specific embodiment, the invention provides method of treating a disease or disorder associated with reduced endogenous testosterone production in a male subject, said method comprising transdermally administering to a skin or mucosal membrane of a male subject a formulation consisting of 1-2% wt of testosterone, 44% wt of ethanol, 20.0% wt of propylene glycol, 5% wt of monoethyl ether of diethylene glycol, 1.2% wt of carbomer, 0.35% wt of triethanolamine, 0.06% wt of edetate disodium and water (q.s.).

In another aspect, the invention provides a transdermal or transmucosal formulation of the invention for use in the treatment of a disease or disorder associated with reduced endogenous testosterone production.

In the context of the invention "diseases and disorders associated with reduced to endogenous testosterone production" should be understood to encompass any disease or disorder which is directly or indirectly related to a condition of a mammalian subject wherein the endogenous production of testosterone is either reduced or substantially non-existent or terminated.

In one embodiment of the invention, diseases and disorders associated with reduced endogenous testosterone production relate to hormonal disorders such as for example hypogonadism, female sexual disorder, hypoactive sexual disorder, and adrenal insufficiency.

In some embodiments, administration of a formulation of the invention decreases the frequency of at least one of the clinical symptoms of a disease or disorder associated with reduced endogenous testosterone production being treated such as hot flashes, night sweats, decreased libido, osteoporosis and so forth.

For human males, diseases and disorders associated with reduced endogenous testosterone production may lead to serum testosterone concentrations of less than a concentration selected from 500 ng/dL, 300 ng/dL, 100 ng/dL, 50 ng/dL and 10 ng/dL. Such conditions include, but are not limited to primary hypogonadism (primary testicular failure) and secondary hypogonadism.

Major causes of primary hypogonadism include: abnormality in the testicles, Klinefelter's syndrome, a congenital abnormality of the sex chromosomes X and Y, undescended testicles, hemochromatosis, high levels of iron in the blood, injury to the testicles, prior hernia surgery, cancer treatment and normal aging.

Major causes of secondary type of male hypogonadism include: defects in the pituitary gland connected to the brain that controls hormone production, impaired testicular function (sometimes caused by defects in the chemical messages from the pituitary gland to the testicles), inflammatory diseases, and the use of certain drugs (such as for example drugs for the treatment of psychiatric disorders and gastro-oesophageal reflux disease) and ageing.

Additional "diseases and disorders associated with reduced endogenous testosterone production" are testosterone deficiency, infertility, impotence, decreased sexual desire, fatigue, loss of energy, mood depression, regression of secondary sexual characteristics, muscle weakness and osteoporosis.

In one embodiment, said disease or disorder associated with reduced endogenous testosterone production is hypogonadism.

In some embodiments, a formulation of the invention is administered to a male mammal in order to provide said mammal with a therapeutically effective dosage of testosterone of about 50 mg/day, thereby providing a male subject with a free serum concentration of testosterone ranging from at least about 300 to about 1000 ng/dL.

In addition to the above, a formulation of the invention may, in some embodiments be administered to a female in need thereof.

In some embodiments, a female undergoing treatment with a formulation of the invention may be of childbearing age or older, in whom androgen production has been interrupted either because of natural menopause, surgical procedures, radiation, chemical ovarian ablation or extirpation, or premature ovarian failure. In addition, a decline in endogenous testosterone in female subjects may be attributed to conditions that suppress adrenal androgen secretion (i.e., acute stress, anorexia nervosa, Cushing's syndrome, and pituitary renal insufficiency), conditions that can decrease ovarian androgen secretion (i.e., ovarian failure and the use of pharmacologic doses of glucocorticoids), and chronic illness such as muscle-wasting diseases like Acquired Immune Deficiency Syndrome (AIDS).

Furthermore, reduced levels of testosterone in female subjects may lead to female sexual dysfunction (FSD) resulting in clinical symptoms such as lack of sex drive, arousal or pleasure, low energy, reduced sense of well-being and osteoporosis. Therefore, some of the results of using a formulation of the invention to treat FSD in female subjects may include one or more of the following: increased energy, increased sense of well-being, decreased loss of calcium from bone, and increased sexual activity and desires.

In pre-menopausal women, total plasma testosterone concentrations generally range from 15-65 ng/dL (free testosterone in pre-menopausal women is approximately 1.5 to 7 pg/ml) and fluctuate during the menstrual cycle, with peaks of androgen concentration corresponding to those of plasma estrogens at the pre-ovulatory and luteal phases of the cycle. In the years leading to postmenopausal transition, levels of circulating androgens begin to decline as a result of age-related reductions of both ovarian and adrenal secretion. There are reports in studies that 24-hour mean plasma testosterone levels in normal pre-menopausal women in their 40's are half that of women in their early 20's. It has been generally accepted, however, that women with androgen deficiency have total plasma testosterone levels less than 25 ng/dL (less than 50-years-old) or less than 20 ng/dL (greater than or equal to 50-years-old) while oophorectomized women can have total plasma testosterone levels less than 10 ng/dL.

In some embodiments a formulation of the invention is administered to a female in order to provide her with a daily therapeutically effective dosage of testosterone of about 1 mg to about 3 mg. In some embodiments a formulation of the invention provides a female subject with a total serum concentration of testosterone from at least about 15 to about 55 ng/dL, or a free serum concentration of testosterone from about 2 to about 7 pg/mL.

In some embodiments of a method of the invention, a formulation of the invention is administered in combination with another treatment, such as, but not limited to, estrogen replacement therapy (ERT), or any other drug or non-medical treatment. Such administration of other therapies may be administered prior to administration of a formulation of the invention, subsequent to administration of a formulation of the invention, or simultaneous with administration of a formulation of the invention, or any other treatment schedule prescribed by a healthcare provider.

In a further aspect the invention provides a kit comprising at least one container comprising a formulation of the invention, and instructions for use thereof.

In some embodiments, a kit of the invention comprises a container which is adapted for dispensing a predetermined measured amount of said formulation.

EXAMPLES

The invention is further described in the following examples, which are not in any way intended to limit the scope of the inventions as claimed.

Example 1

Preparation of Testosterone Gel Formulations 1% wt and 2% wt

The 1% wt and 2% wt testosterone formulations were prepared by methods known in the art, as schematically shown in FIG. 1. The preparation was carried out in controlled environment under continuous vacuum and nitrogen blanketing with temperature control into a stainless steel planetary mixer.

Table 1 demonstrates a 10-kg batch preparation of a 1% wt testosterone gel formulation. Table 2 demonstrates a 10-kg batch preparation of a 2% wt testosterone gel formulation.

TABLE 1

Batch Formula of Testosterone Gel 1%

Batch Size: 10 kg

| Component | Amount per batch |
|---|---|
| Testosterone | 100.0 g |
| Ethanol 96% v/v (expressed as ethanol, anhydrous) | 4400 g |
| Propylene glycol | 2000 g |
| Diethylene glycol monoethyl ether | 500 g |
| Carbomer 980 | 120 g |
| Trolamine | 35 g |
| Edetate disodium | 6 g |
| Purified water | up to 10 kg |

TABLE 2

Batch Formula of Testosterone Gel 2%

Batch Size: 10 kg

| Component | Amount per batch |
|---|---|
| Testosterone | 200.0 g |
| Ethanol 96% v/v (expressed as ethanol, anhydrous) | 4400 g |
| Propylene glycol | 2000 g |
| Diethylene glycol monoethyl ether | 500 g |
| Carbomer 980 | 120 g |
| Trolamine | 35 g |
| Edetate disodium | 6 g |
| Purified water | up to 10 kg |

All experiments herein below were performed using formulations prepared essentially as described in Example 1.

A. IN VITRO EXAMPLES

General Protocol and Measurements

All in vitro experiments were performed using fresh skin pieces (pig ear, human skin) mounted on standard Franz-type vertical diffusion cells (Hanson Research Inc.).

Drug loading was approximately 5.6 mg gel/cm$^2$ (as per OECD guidance no. 28, Paris, December 2000), except indicated otherwise.

Temperature was maintained at 35° C. throughout the duration of the skin permeation study (24 hours).

Cumulative drug amounts permeated over 24 hours (µg/cm$^2$) were determined by High Pressure Liquid Chromatography techniques.

Example 2

Effect of Alcohol Concentration on Penetration of Testosterone

Table 1 below provides the formulations used for assessing the effect of the alkanol levels on the penetration of a testosterone formulation of the invention.

TABLE 3

Testosterone formulations used in Example 1

| Component | Formulation 1 | Formulation 2 |
|---|---|---|
| Testosterone | 1.00% wt | 1.00% wt |
| Ethanol, anhydrous | 53.0% wt | 69.0% wt |
| Carbomer 980 | 1.20% wt | 1.20% wt |
| Edetate disodium | 0.06% wt | 0.06% wt |
| Trolamine | 0.35% wt | 0.35% wt |
| Purified water | up to 100% wt | up to 100% wt |

Figure 2A:
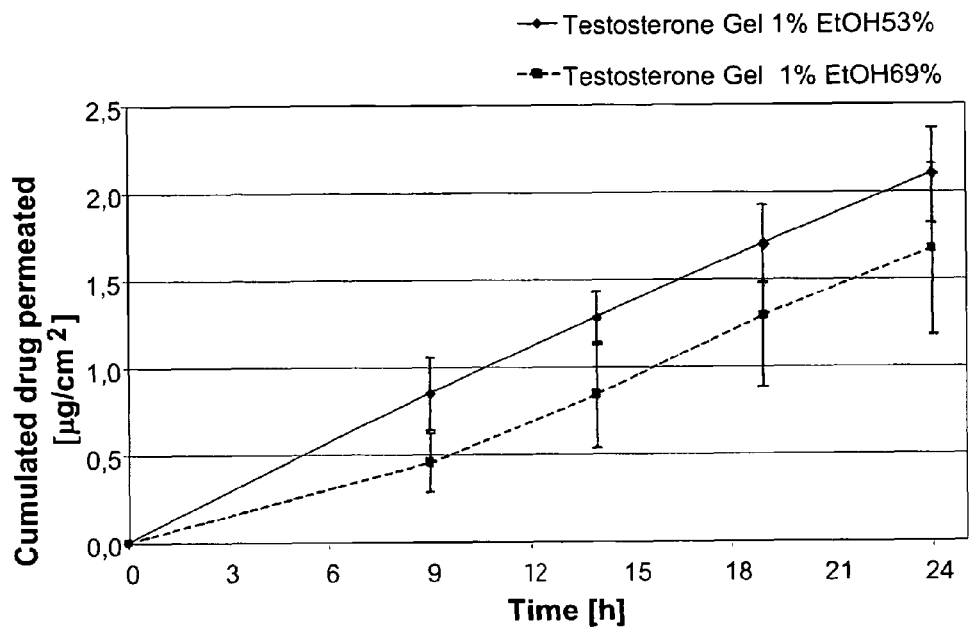
FIGS. 2A-2B show the cumulated penetration profile (absolute kinetic profile, in $\mu g/cm^2$, FIG. 2A) and the drug flux (in $\mu g/cm^2 h$, FIG. 2B) of testosterone (see example 2).
Figure 2B:
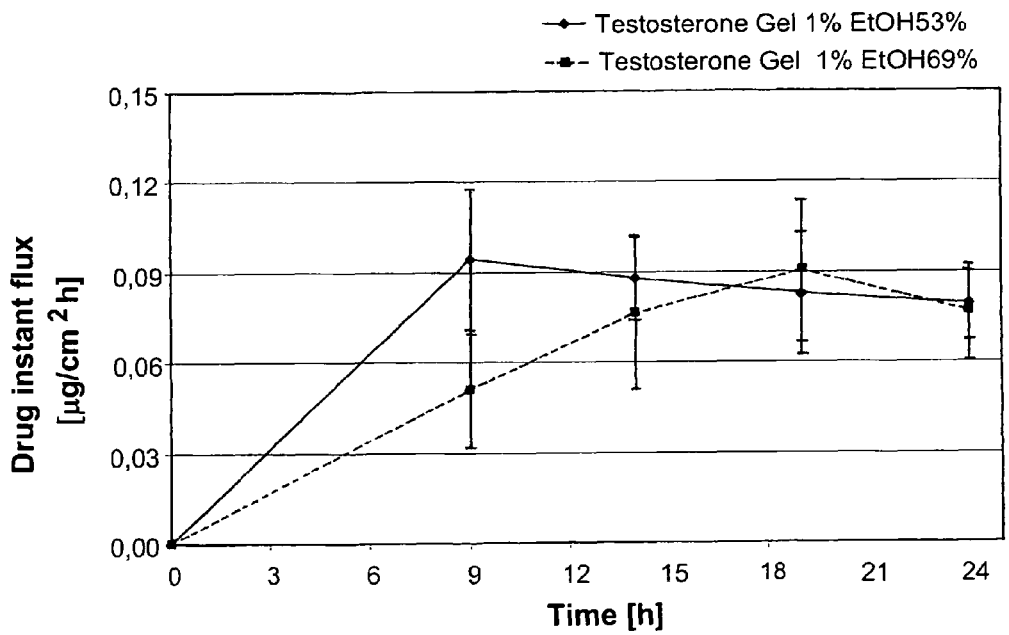
Figure 3A:
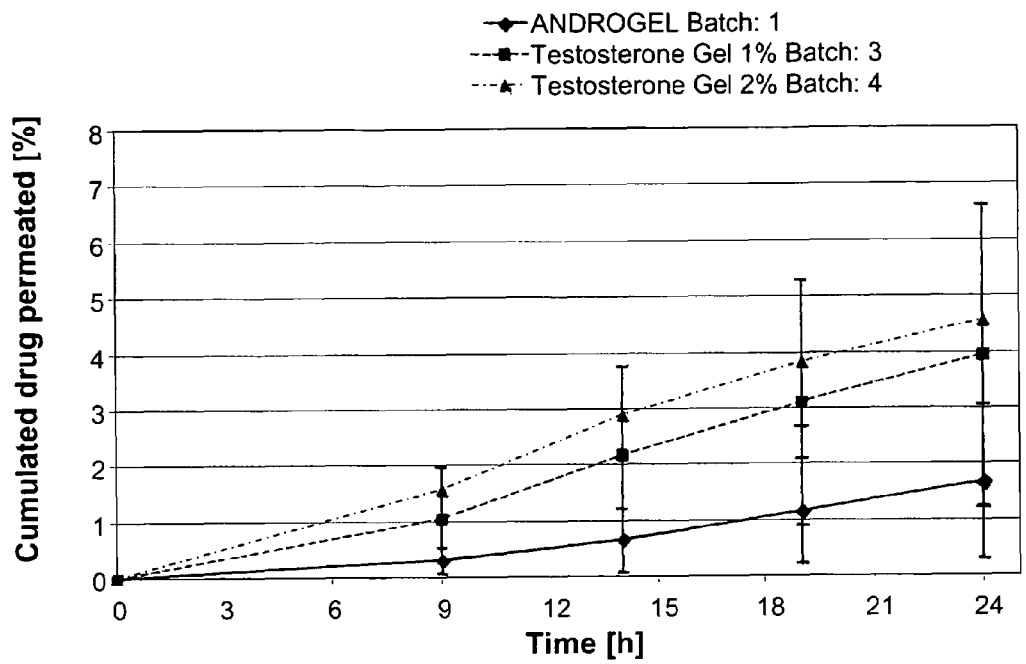
FIGS. 3A-3B show the cumulated penetration profile (absolute kinetic profile, in $\mu g/cm^2$, FIG. 3A) and the drug flux (in $\mu g/cm^2 h$, FIG. 3B) of testosterone formulations in in vitro study #1 (see example 3).
Figure 3B:
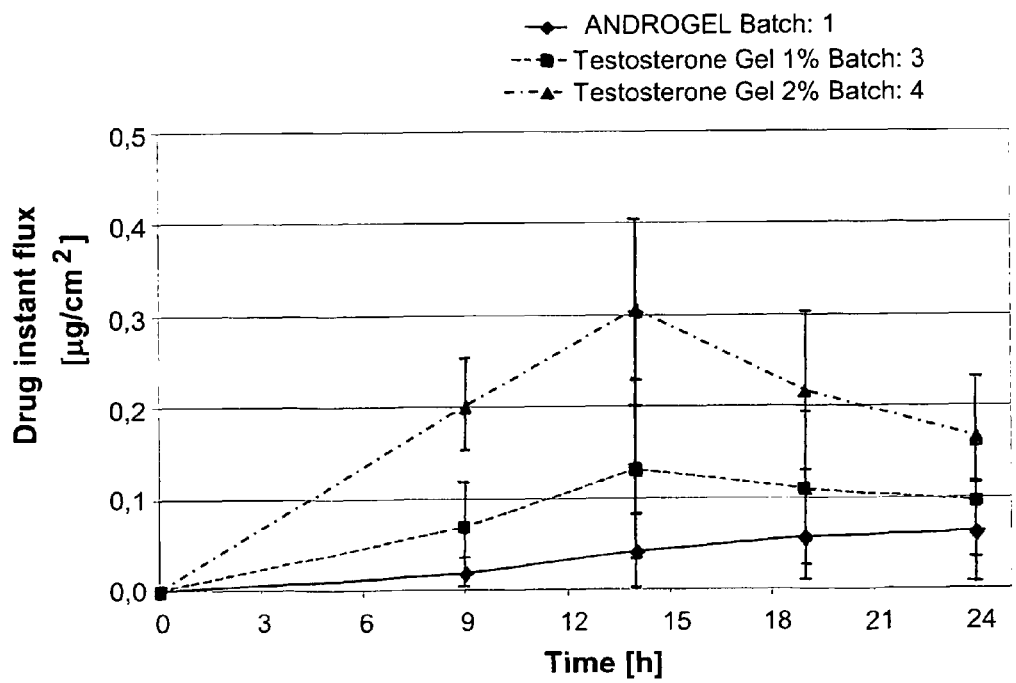
Figure 4A:
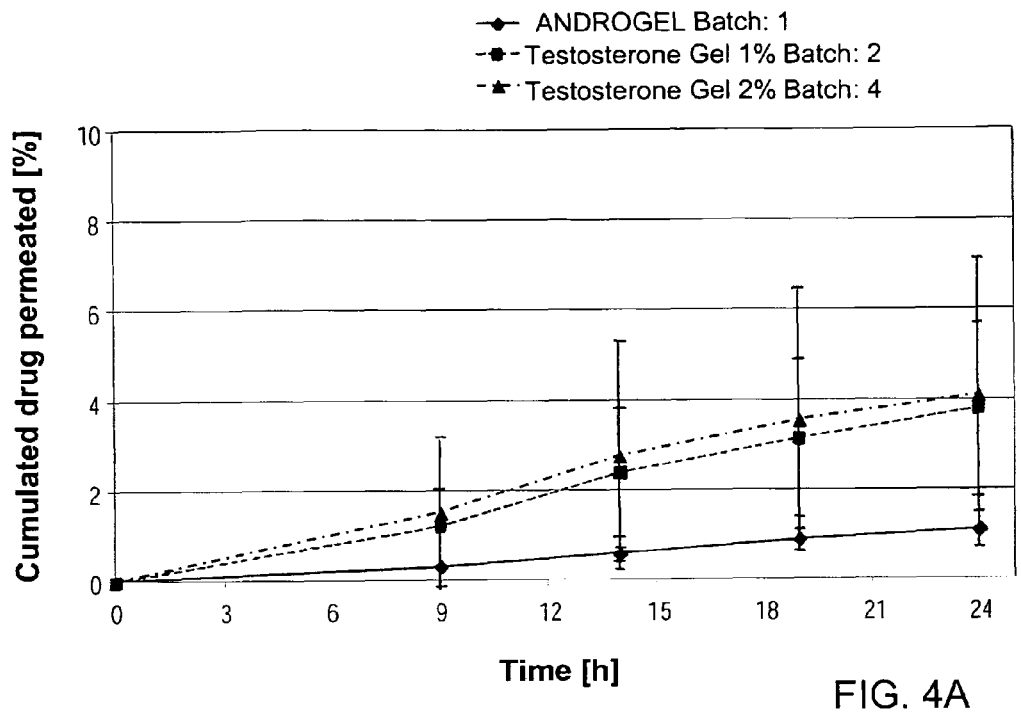
FIGS. 4A-4B show the cumulated penetration profile (absolute kinetic profile, in $\mu g/cm^2$, FIG. 4A) and the drug flux (in $\mu g/cm^2 h$, FIG. 4B) of testosterone formulations in in vitro study #2 (see example 3).
Figure 4B:
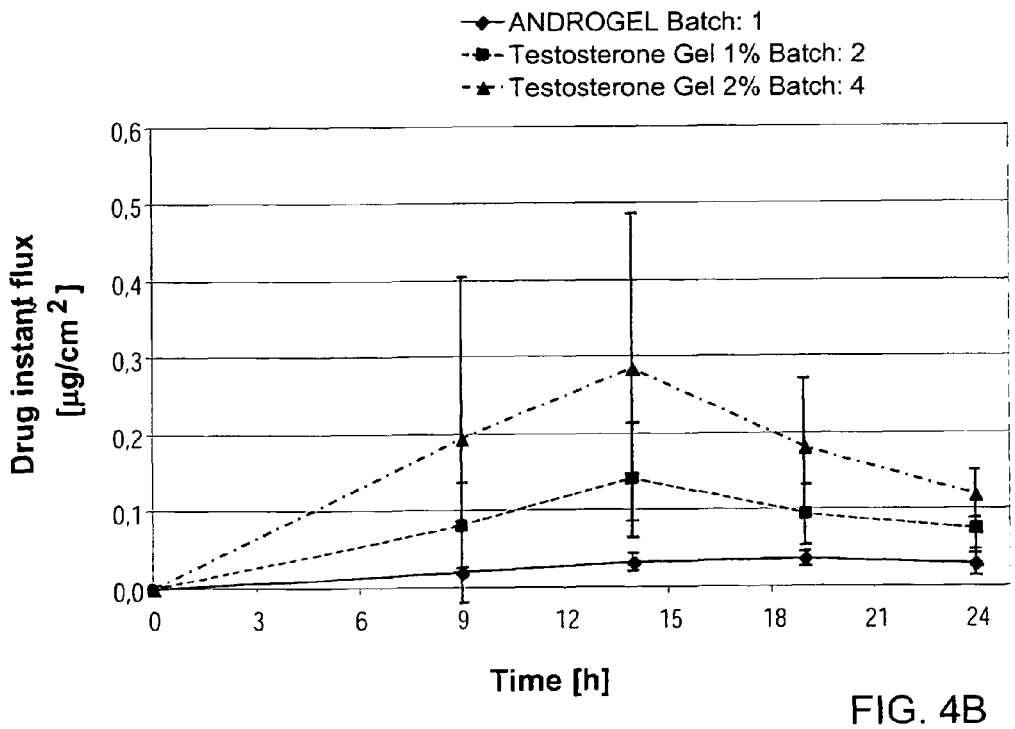
Figure 5A:
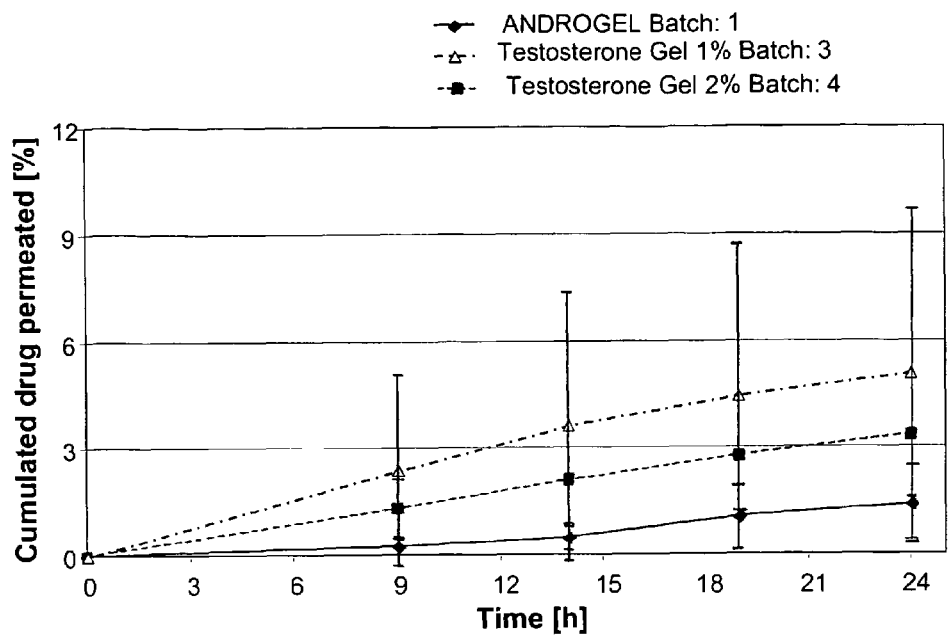
FIGS. 5A-5B show the cumulated penetration profile (absolute kinetic profile, in $\mu g/cm^2$, FIG. 5A) and the drug flux (in $\mu g/cm^2 h$, FIG. 5B) of testosterone formulations in in vitro study #3 (see example 3).
Figure 5B:
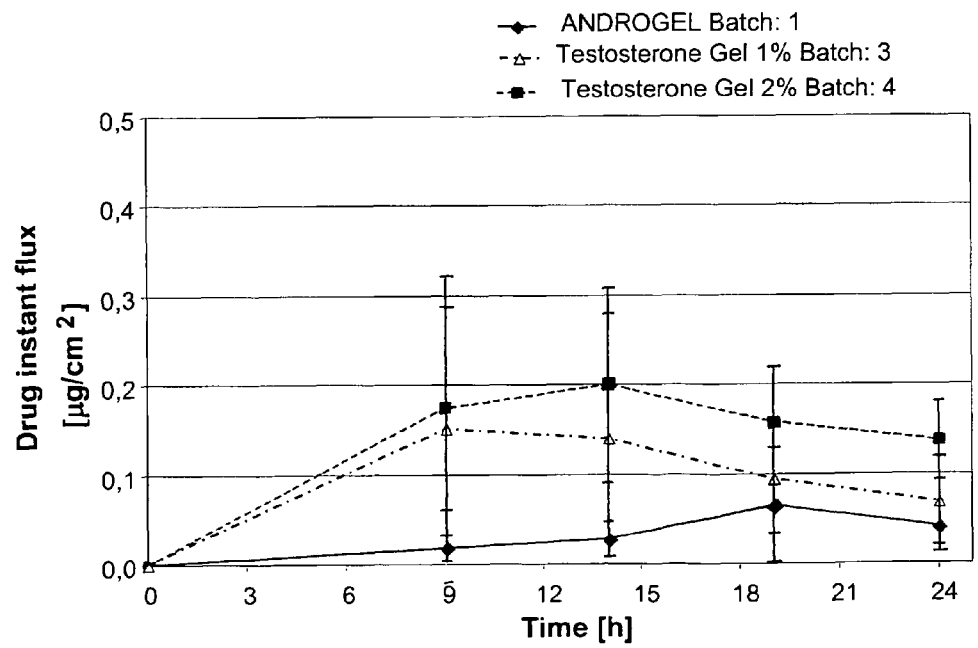
Figure 6A:
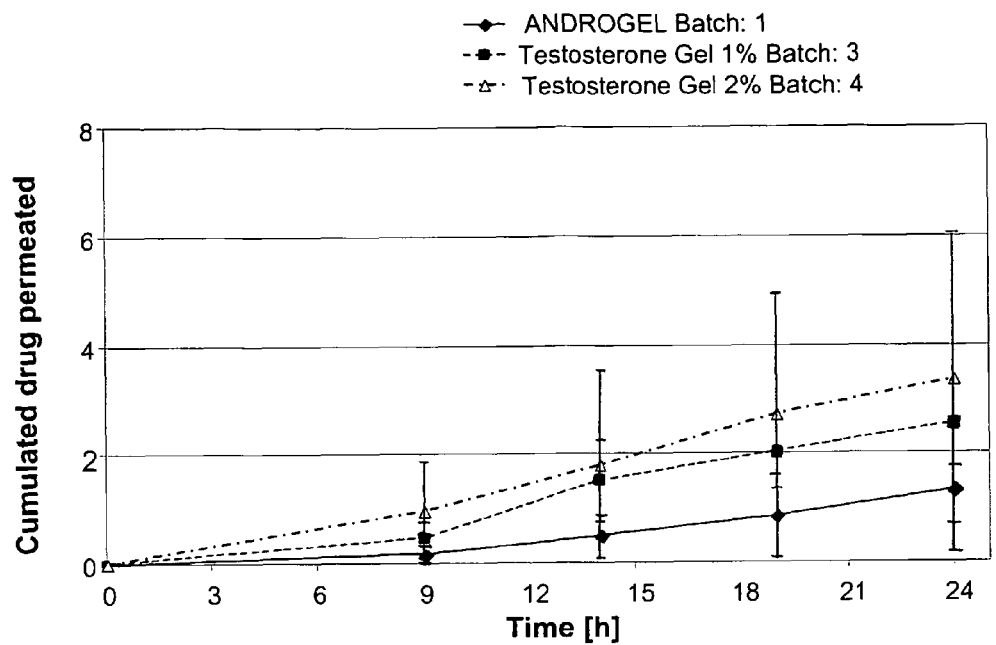
FIGS. 6A-6B show the cumulated penetration profile (absolute kinetic profile, in $\mu g/cm^2$, FIG. 6A) and the drug flux (in $\mu g/cm^2 h$, FIG. 6B) of testosterone formulations in in vitro study #4 (see example 3).
Figure 6B:
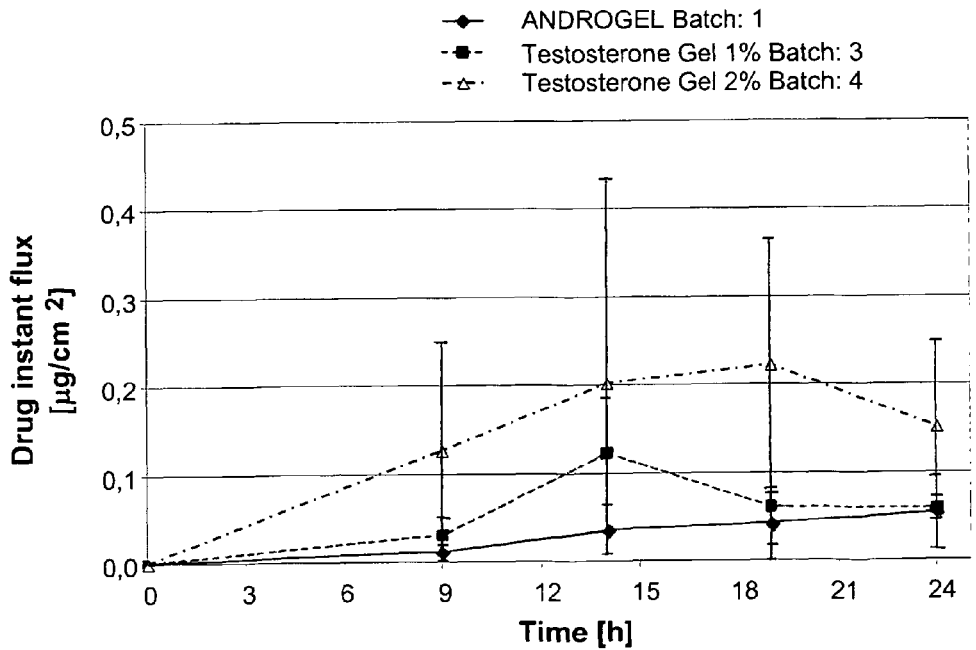
Figure 7A:
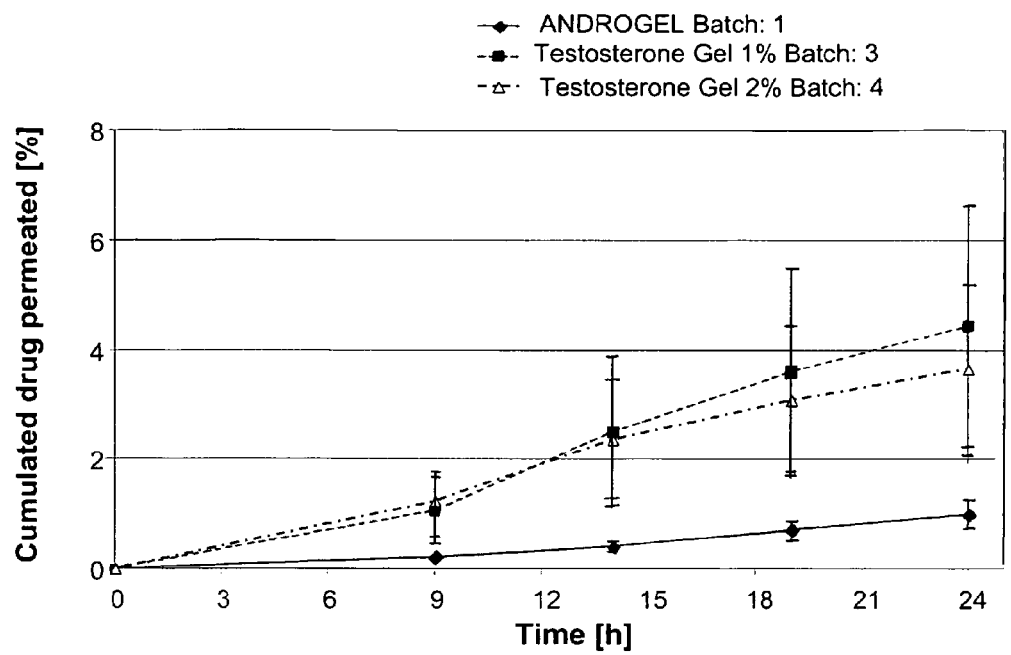
FIGS. 7A-7B show the cumulated penetration profile (absolute kinetic profile, in $\mu g/cm^2$, FIG. 7A) and the drug flux (in $\mu g/cm^2 h$, FIG. 7B) of testosterone formulations in in vitro study #5 (see example 3).
Figure 7B:
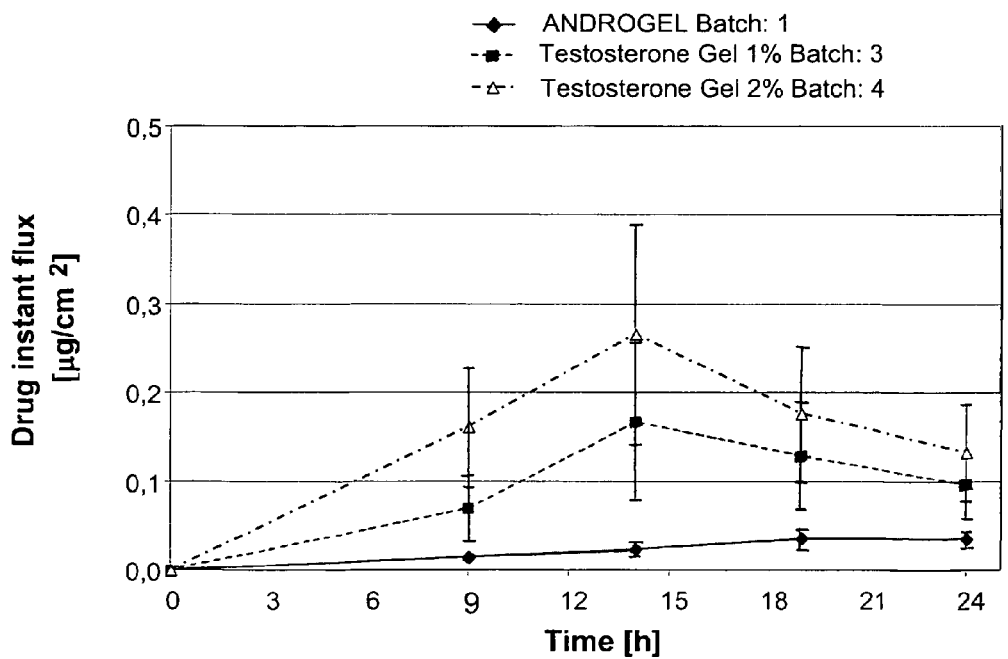
Figure 8A:
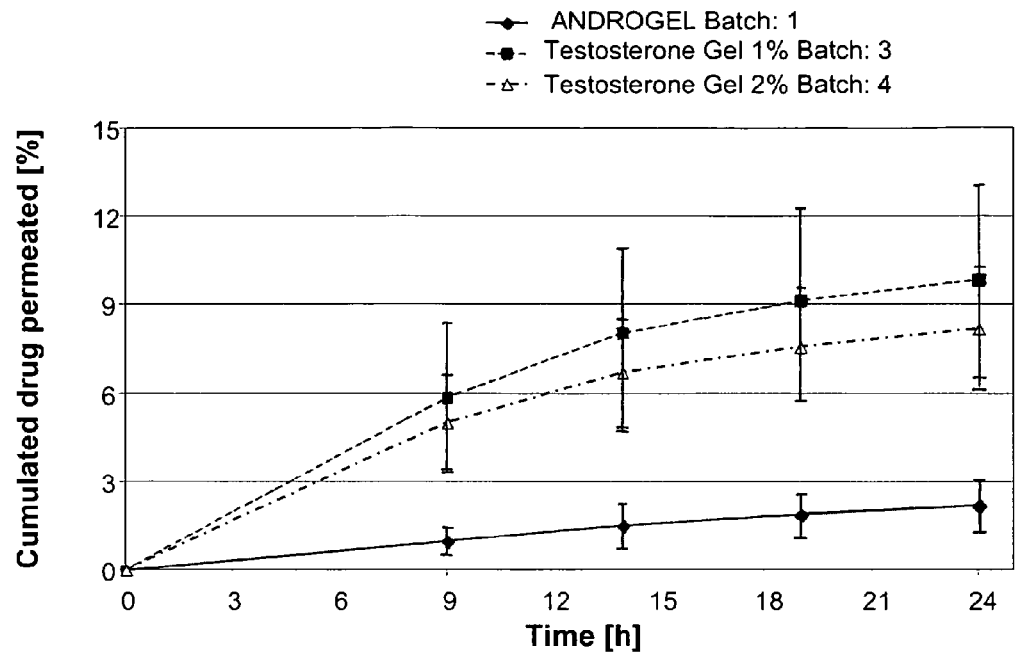
FIGS. 8A-8B show the cumulated penetration profile (absolute kinetic profile, in $\mu g/cm^2$, FIG. 8A) and the drug flux (in $\mu g/cm^2 h$, FIG. 8B) of testosterone formulations in in vitro study #6 (see example 3).
Figure 8B:
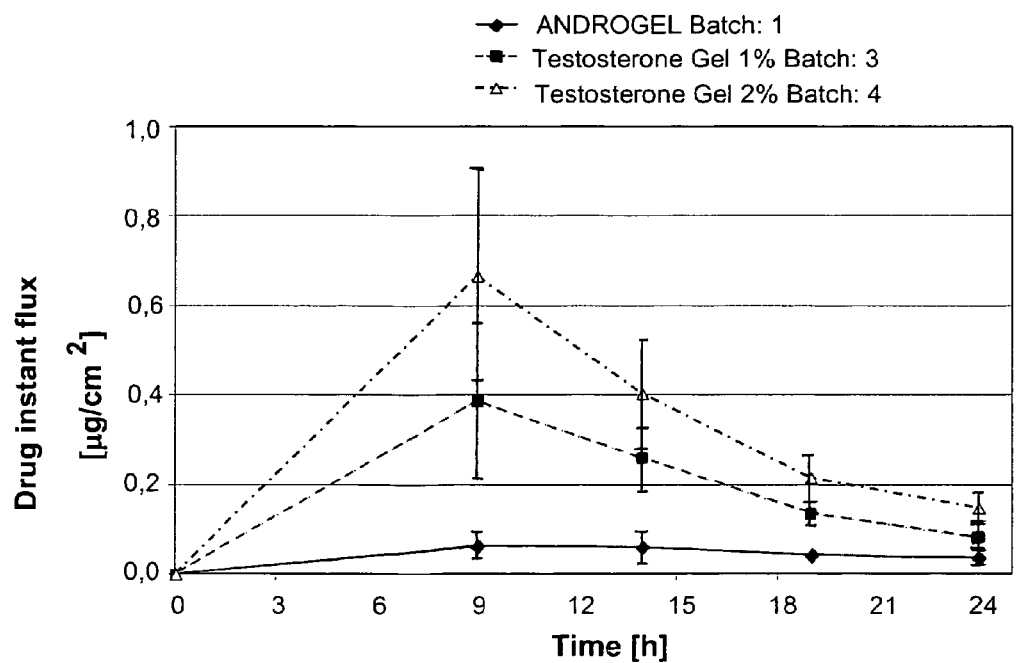

FIGS. 2A-2B show the cumulated penetration profile (absolute kinetic profile, FIG. 2A) and the drug flux (FIG. 2B) of testosterone. These results suggest that there is no need to increase ethanol concentration above approximately 50% wt, a level beyond which increasing ethanol concentration does not result in skin penetration enhancement. Additionally, ethanol levels higher than about 50% w/w may cause severe side effects such as skin sensitization (skin dryness, redness, and itching), especially in cases where the topical application is chronic, e.g. once-daily for several months to several years.

Example 3

Effect of Penetration Enhancing System

Different concentrations of the components of the permeation enhancing system (comprising ethanol, propylene glycol and DGME) comprised in formulations of the invention were tested for optimized maximal absorption of testosterone through the skin. Tables 4 and 5 below list the formulations tested. These formulations were compared with the absorption observed for the product ANDROGEL®.

TABLE 4

Formulation Components (Results shown in FIGS. 3-8, for Studies #1-6 respectively)

| Components | ANDROGEL ® Batch 1 | Testosterone Gel 1% Batch 2 | Testosterone Gel 1% Batch 3 | Testosterone Gel 2% Batch 4 |
|---|---|---|---|---|
| Testosterone | 1.00% wt | 1.00% wt | 1.00% wt | 2.00% wt |
| Ethanol, anhydrous | 67.0% wt | 47.5% wt | 44.0% wt | 44.0% wt |
| Isopropyl myristate | 0.50% wt | — | — | — |
| DGME | — | 5.00% wt | 5.00% wt | 5.00% wt |
| Propylene glycol | — | 20.0% wt | 20.0% wt | 20.0% wt |
| Carbomer C980 | 0.90% wt | 1.20% wt | 1.20% wt | 1.20% wt |
| Sodium hydroxide | 4.72% wt | — | — | — |
| Trolamine | — | 0.35% wt | 0.35% wt | 0.35% wt |
| Edetate disodium | — | 0.06% wt | 0.06% wt | 0.06% wt |
| Purified water | up to 100% wt | up to 100% wt | up to 100% wt | up to 100% wt |

In vitro skin permeation studies #1-6 are shown in FIGS. 3 to 8 and are also summarized in Tables 5 and 6 below:

TABLE 5

Cumulated testosterone permeated [%] after 24 hours

| Study # | #1 | #2 | #3 | #4 | #5 | #6 |
|---|---|---|---|---|---|---|
| ANDROGEL ® | 1.67 | 1.11 | 1.40 | 1.31 | 1.00 | 2.17 |
| Testosterone Gel 1% | 3.93 | 3.76 | 3.34 | 2.55 | 4.42 | 9.82 |
| Testosterone Gel 2% | 4.56 | 4.07 | 5.06 | 3.37 | 3.65 | 8.21 |

TABLE 6

Maximal testosterone instant flux [mg/cm$^2$h]

| Study # | #1 | #2 | #3 | #4 | #5 | #6 |
|---|---|---|---|---|---|---|
| ANDROGEL ® | N/A | 0.04 (19 H) | 0.07 (19 H) | N/A | N/A | 0.07 (9 H) |
| Testosterone Gel 1% | 0.13 (14 H) | 0.14 (14 H) | 0.15 (9 H) | 0.12 (14 H) | 0.17 (14 H) | 0.39 (9 H) |
| Testosterone Gel 2% | 0.31 (14 H) | 0.28 (14 H) | 0.20 (14 H) | 0.22 (19 H) | 0.27 (14 H) | 0.67 (9 H) |

The results of in vitro study #1 (FIGS. 3A-3B and Tables 5 and 6) show that at 1% testosterone strength (Table 4, batch 3), the penetration enhancing system of the formulation enabled a skin penetration of testosterone which is 2.4-fold higher than skin penetration of ANDROGEL® (Table 4, batch 1). Doubling testosterone strength (from 1% wt to 2% Table 4, batch 4) led to a further 2.3-fold increase of skin penetration of testosterone.

The results of in vitro study #2 (FIGS. 4A-4B and Tables 5 and 6) show that the use of a penetration enhancing system (Table 4, batches 2 and 4) as defined herein above provides improved skin penetration results as compared with the ANDROGEL® (Table 4, batch 1). Doubling the testosterone strength from 1% wt to 2% wt and lowering the concentration of the alkanol (from 47.5% wt in batch 2 to 44% wt in batch 3) provided enhanced penetration results.

The results of in vitro studies #3-6 (FIGS. 5-8 and Tables 5 and 6) show that the use of a penetration enhancing system (Table 4, batch 3) as defined herein above provides improved skin penetration results as compared with the ANDROGEL® (batch 1). Doubling the testosterone strength (from 1% wt in batch 3 to 2% wt in batch 4) provided enhanced instant testosterone flux results (Table 6 and FIGS. 5B, 6B, 7B and 8B).

Example 4

Effect of Dose Volume on Testosterone Penetration

The following formulations were tested for in vitro testosterone penetration:

Testosterone gel 1%, 10 mg gel (0.1 mg testosterone) applied per cell.

Testosterone gel 1%, 20 mg gel (0.2 mg testosterone) applied per cell.

Testosterone gel 2%, 10 mg gel (0.2 mg testosterone) applied per cell.

All formulations contained the following additional components: 44.0% wt of ethanol, 20.0% wt of propylene glycol, 5.0% wt of diethylene glycol monoethyl ether, 1.20% wt of carbomer C980 NF, 0.35% wt of triethanolamine, 0.06% wt of edetate disodium and water (q.s.).

Each test formulation was tested in 4 replicates (4 different skin donors). Overall, twelve skin samples were used. Thickness of each sample was measured with a micrometer. The samples were consequently mounted on vertical glass Franz diffusion cells with a receptor compartment of about 7.5 mL, a donor compartment of 3.0 mL and a diffusion area of 1.77 cm$^2$.

Phosphate buffered saline (PBS) at pH 7.4 with addition of 2% w/v oleth-20, i.e. oleyl ether of polyoxyethylene glycol (VOLPO™ 20 or BRIJ™ 98, now BRIJ™ O20), was used as receptor solution, maintained at 35° C. during the whole study, and stirred at 600 RPM. The study was performed using a Microette® autosampler. After 2 hours pre-incubation of the skin samples with the receptor solution, and integrity assessment by evaporimetry, about 10 mg (5.65 mg/cm$^2$) or 20 mg (11.3 mg/cm$^2$) of the tested formulation was applied with the tip of a plastic syringe plunger and gently spread over the diffusion surface. Diffusion of the drug was allowed in non-occluded conditions during 24 hours. Receptor solution samples (1.2 mL) were removed after 9 hours, 14 hours, 19 hours, and 24 hours (after 0.8 mL receptor compartment priming). The samples were collected in 2 mL HPLC amber glass vials pre-sealed with septum crimp-caps and pre-filled with 10 μL of a solution of trifluoroacetic acid (TFA) 10%. Then samples were transferred into Eppendorf microtubes, and were centrifuged at 13500 RPM (SIGMA 2-16 P centrifuge) during 10 min. Each supernatant (0.9 mL) was transferred in a 2 mL HPLC amber glass vial. Analysis of the samples was performed by HPLC.

Figure 9:
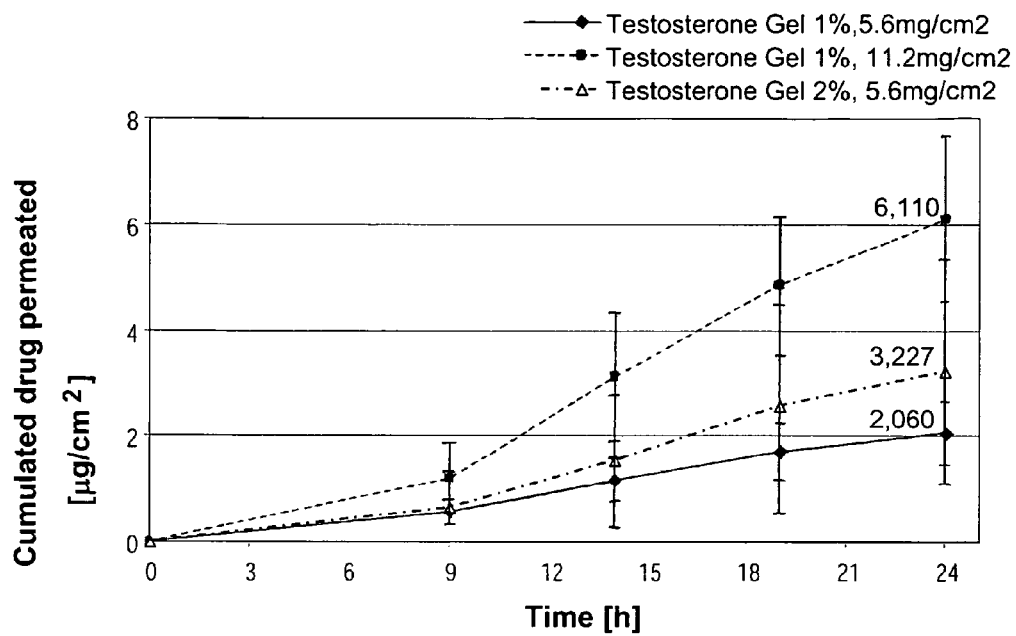
FIG. 9 shows the cumulated penetration profile of testosterone formulations tested (absolute kinetic profile, in $\mu g/cm^2$) in example 4.

FIG. 9 shows that the 2% sample provided superior skin permeation of testosterone compared to the 1% sample when keeping the same gel loading per unit area (5.6 mg/cm$^2$):

(i) the absolute cumulated amount of testosterone permeated after 24 hours was 1.6 times higher (3.227 μg/cm$^2$ versus 2.06 μg/cm$^2$) with the 2% sample;

(ii) the maximal testosterone instant flux was 1.7 times higher (0.209 μg/cm$^2$ versus 0.123 μg/cm$^2$) with the 2% sample;

(iii) the testosterone instant flux at 24 hours was 1.9 times higher (0.130 μg/cm$^2$ versus 0.070 μg/cm$^2$) with the 2% sample;

FIG. 9 further shows that doubling the amount of T Gel 1% applied per cm$^2$ from about 5.6 mg/cm$^2$ to about 11.2 mg/cm$^2$, i.e. when doubling the amount of testosterone applied per cm$^2$ from about 56 μg/cm$^2$ to about 112 μg/cm$^2$, the absolute cumulated amount of testosterone permeated after 24 hours was almost tripled (6.11 μg/cm$^2$ versus 2.06 μg/cm$^2$).

Figure 10:
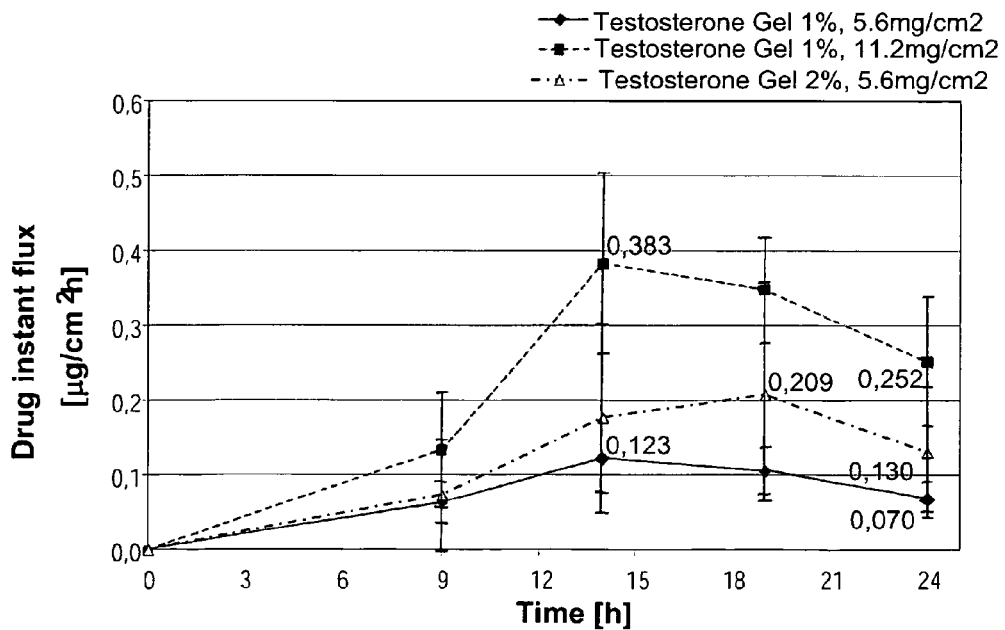
FIG. 10 shows the drug flux (in $\mu g/cm^2 h$) of testosterone formulations tested in example 4.

FIG. 10 shows that the maximum testosterone flux of penetration when loading 10 mg of the 2% sample applied over 1.77 cm$^2$ (2% testosterone/5.6 mg/cm$^2$) was obtained after 19 hours whereas the maximum testosterone flux of penetration when loading 20 mg of the 1% sample applied over 1.77 cm$^2$ (1% testosterone/11.2 mg/cm$^2$) was obtained after 14 hours. This was all the more surprising because FIG. 10 also shows that increasing testosterone loading of the 1% sample from 5.6 μg/cm$^2$ to 11.2 μg/cm$^2$ did not affect the time at which the maximal instant flux occurred (14 hours).

Example 5

Effect of Propylene Glycol Concentration on Testosterone Penetration

The following formulations were tested for in vitro testosterone penetration:
Testosterone gel 1%, containing 15% wt propylene glycol.
Testosterone gel 1%, containing 20% wt propylene glycol.
Testosterone gel 2%, containing 15% wt propylene glycol.
Testosterone gel 2%, containing 20% wt propylene glycol.

All formulations contained the following additional components: 44.0% wt of ethanol, 20.0% wt of propylene glycol, 5.0% wt of diethylene glycol monoethyl ether, 1.20% wt of carbomer C980 NF, 0.35% wt of triethanolamine, 0.06% wt of edetate disodium and water (q.s.).

Each test formulation was tested in 3 replicates (3 different skin donors). Overall, twelve skin samples were used. The testing protocol was identical to that described in Example 4.

Figure 11:
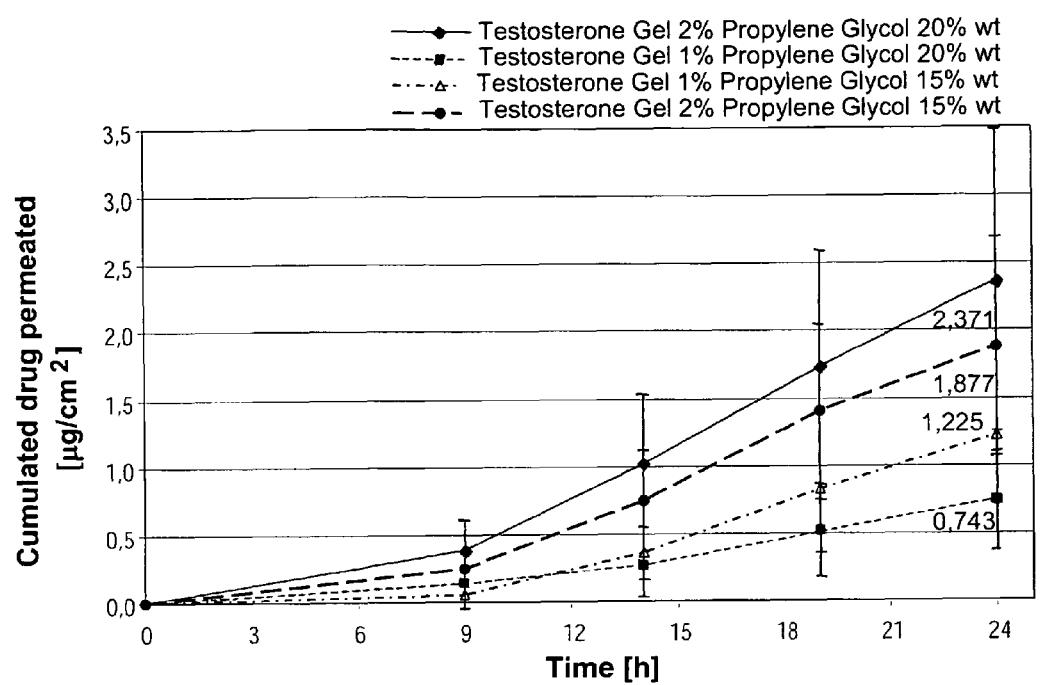
FIG. 11 shows the cumulated penetration profile of testosterone formulations (absolute kinetic profile, in $\mu g/cm^2$) tested in example 5.

FIG. 11 shows that cumulated delivery of testosterone through the skin after 24 hours was 1.225 μg/cm$^2$ with 1% testosterone gel containing 15% wt propylene glycol versus 0.743 μg/cm$^2$ with 1% testosterone containing 20% wt propylene glycol.

FIG. 11 most surprisingly shows that opposite thereto, increasing the concentration of propylene glycol from 15% wt to 20%, respectively, in the 2% wt testosterone gel led to an unexpected increase of cumulated delivery of testosterone through the skin after 24 hours: 1.877 μg/cm$^2$ versus 2.371 μg/cm$^2$, respectively.

B. IN VIVO EXAMPLES

Example 6

In Vivo Study of Testosterone Transdermal Formulations in Human Males

The testosterone gel formulations produced essentially as described in Example 1, were assessed in vivo as follows. The objectives of the in vivo study were to determine the relative bioavailability, pharmacokinetic profile and assess the safety and tolerability of transdermal testosterone gel formulations comprising 1% and 2% testosterone after single and repeated transdermal administrations to healthy men for 7 days of repeated dosing, as compared with TESTOGEL/ANDROGEL® (containing 1% testosterone gel for transdermal application, manufactured by Laboratories Besins International).

Ten (10) healthy male subjects were included in the study, 18-45 years of age. The study included three randomized treatment periods of each 7 days with a 6-9 day wash-out period in between, as follows:

Treatment period A: a subject was administered the 1% wt testosterone gel,

Treatment period B: the same subject was administered the 2% wt testosterone gel, Treatment period C: the same subject was administered with ANDROGEL®.

Before inclusion into the study, all subjects underwent general physical examination, including vital signs, 12-lead ECG, and laboratory assessment including haematology, clinical chemistry (including PSA), haemostasis and urinalysis. To ensure that the subjects had low levels <1 ng/mL of endogenous testosterone, subjects received two doses (3.75 mg) of the GnRH agonist DECAPEPTYL N®, in order to suppress the endogenous production of testosterone. DECAPEPTYL N® (triptorelin 3.75 mg 1 month depot) was provided as a pre-filled syringe with powder and 1 mL of solvent for suspension. DECAPEPTYL N® was suspended in 1 mL, giving a concentration of 3.75 mg/mL of which 1 mL was injected in the gluteal muscle. The first dose of DECAPEPTYL N® was administered on Day −21 and the second dose was administered 28 days later, i.e. on Day 8 of the first treatment period.

The subjects came for residential stays on Days 1 and 7 in each treatment period. In addition, the subjects came for ambulatory visits on Days 3 to 6. Between treatment periods there was a wash-out period of 6-9 days. A follow-up visit was conducted 14 days after the last treatment period to ensure that the level of testosterone has returned to normal. LH was measured on Day −1 and on Days 1 to 8 in each treatment period in order to detect if any subject escaped down regulation during treatment.

A dose of 5 g of the testosterone gel 1%, a dose of 2.5 g of testosterone gel 2% or 5 g of ANDROGEL®, were administered in each treatment period, to the same 1000 cm² area of the abdomen once daily for 7 days during each treatment period. The dose was applied to the area until the gel was completely absorbed. The application site was allowed to dry before covered with clothes.

Blood/serum samples were collected as follows in each treatment period on:

Day 1: Pre-dose (0) (i.e. prior to the administration of the first dose) and thereafter on 2, 4, 6, 8, 12, and 16 hours after the first dose.

Days 2-6: Pre-dose only

Day 7: Pre-dose, 2, 4, 6, 8, 12, 16, 24, and 48 (day 8) hours after the last administration.

The testosterone concentration in the serum samples was quantified using known methods, using supported liquid extraction by quantification using ultra performance liquid chromatography with mass spectrometric detection (UPLC-MS/MS).

Pharmacokinetic (PK) parameters were estimated using non-compartmental analysis. PK parameters were calculated based on measurements from Day 1 to Day 2, and from Day 7 to Day 8. PK parameters $AUC_\tau$ and $C_{max}$ were compared across treatment groups using an ANOVA model for the log-transformed values. The ratio of the PK parameters was estimated along with 90% confidence limits. Analysis of testosterone and radio-labelled $^2H_3$-Testosterone was carried out using a UPLC-MS/MS system.

Table 7 below presents the mean and standard deviation (SD) in vivo testosterone concentration results of 1% wt and 2% wt testosterone gel formulations and of ANDROGEL. Table 8 shows the $C_{max}$ and $AUC_\tau$ results for the two tested formulations and ANDROGEL.

TABLE 8

PK values of final dose (s.s)

|  | $AUC_\tau$ (ng*hr/dL) | SD | RSD | $C_{max}$ (ng/dL) | SD | RSD |
|---|---|---|---|---|---|---|
| Testosterone Gel 1% | 6691.38 | 2452.2 | 36.6% | 602.3 | 284.7 | 47.3% |
| Testosterone Gel 2% | 4822.54 | 1757.4 | 36.4% | 316.9 | 98.1 | 31.0% |
| ANDROGEL ® | 3631.05 | 1409.9 | 38.8% | 231.1 | 93.5 | 40.4% |

The data presented show that the 2% formulation provides more sustained and controlled plasma levels over all time points with significant less $C_{max}$ values. In addition the 2% testosterone gel provides less relative variability judged by the SD obtained.

Figure 12:
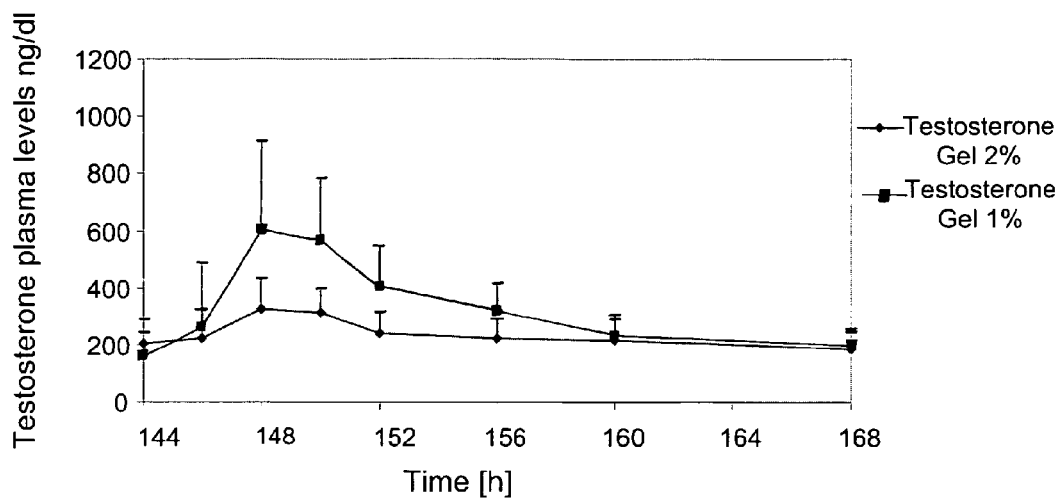
FIG. 12 shows the in vivo testosterone plasma levels of a 2% wt testosterone formulation compared to a 1% wt testosterone formulation over a period of 24 h after the last dosing (day 7) of each formulation in a treatment period (see example 6).

FIG. 12 shows the daily plasma profile at steady state in the down-regulated males for the two testosterone gel formulations tested after the last administration, i.e. at 168 hours until 192 hours (see Table 7) with each formulation. Testosterone plasma levels following daily administration of 2.5 g of testosterone gel 2% (50 mg testosterone daily) for seven days was shown to be more controlled with less fluctuations than the testosterone plasma levels following daily administration of 5 g of testosterone gel 1% (50 mg testosterone daily).

Additionally, peak value ($C_{max}$) was found to be lower for the 2% wt testosterone gel than for the 1% wt testosterone gel. The in viva variability of $C_{max}$ was less pronounced for the 2% wt testosterone gel than for the 1% wt testosterone gel (RSD of 31.0%, versus 47.3%: see Table 8), whereas the in vivo variability of $AUC_\tau$ was similar for both testosterone gel strengths (about 36%).

TABLE 7

In vivo testosterone concentrations (ng/dL) for 1% wt and 2% wt formulations and ANDROGEL ®

| Day of treatment | Time (h) | Testosterone Gel 1% Mean | SD | Testosterone Gel 2% Mean | SD | ANDROGEL ® Mean | SD |
|---|---|---|---|---|---|---|---|
| 0 (Pre-dose) | 0 h | 42.66 | 40.13 | 34.04 | 27.54 | 32.41 | 24.22 |
| 0 | 2 h | 127.46 | 120.87 | 101.43 | 41.59 | 57.81 | 39.24 |
| 0 | 4 h | 527.20 | 338.79 | 313.10 | 112.32 | 86.18 | 40.21 |
| 0 | 6 h | 553.70 | 231.06 | 281.40 | 71.24 | 107.74 | 48.55 |
| 0 | 8 h | 391.70 | 175.98 | 199.20 | 34.05 | 104.67 | 61.09 |
| 0 | 12 h | 271.20 | 83.86 | 169.80 | 20.84 | 147.58 | 96.93 |
| 0 | 16 h | 213.00 | 48.65 | 152.90 | 27.85 | 139.78 | 46.63 |
| Day 1 | 24 h | 184.80 | 54.96 | 157.70 | 59.02 | 155.55 | 40.47 |
| Day 2 (Pre-dose) | 48 h | 205.20 | 87.46 | 126.22 | 68.30 | 157.29 | 84.15 |
| Day 3 (Pre-dose) | 72 h | 168.37 | 67.96 | 149.22 | 81.85 | 152.80 | 68.61 |
| Day 4 (Pre-dose) | 96 h | 124.74 | 62.19 | 139.03 | 55.61 | 178.51 | 110.18 |
| Day 5 (Pre-dose) | 120 h | 135.00 | 56.66 | 162.46 | 73.82 | 155.03 | 73.18 |
| Day 6 (Pre-dose) | 144 h | 160.82 | 86.87 | 204.90 | 83.54 | 188.89 | 107.25 |
| Day 6 + 2 h | 146 | 256.80 | 232.08 | 222.80 | 101.40 | 167.52 | 87.14 |
| Day 6 + 4 h | 148 | 604.10 | 312.83 | 326.30 | 105.58 | 195.42 | 90.57 |
| Day 6 + 6 h | 150 | 565.20 | 220.35 | 316.40 | 81.68 | 178.08 | 61.26 |
| Day 6 + 8 h | 152 | 402.00 | 147.53 | 242.40 | 76.59 | 184.28 | 77.23 |
| Day 6 + 12 h | 156 | 320.60 | 95.44 | 225.50 | 64.60 | 190.76 | 74.35 |
| Day 6 + 16 h | 160 | 235.70 | 54.44 | 219.60 | 85.93 | 165.68 | 54.23 |
| Day 7 | 168 | 199.90 | 60.35 | 189.20 | 61.53 | 207.00 | 58.75 |
| Day 8 | 192 | 92.24 | 42.48 | 133.61 | 70.04 | 103.68 | 59.10 |

Thus, administration of 2% wt testosterone gel resulted in a more regulated testosterone plasma level with less variations compared to administration of 1% wt testosterone gel. Thus, 2% wt testosterone gel provided a more steady therapeutic effect resulting in less side effects than 1% wt testosterone gel.

Example 7

In order to achieve equivalent plasma levels as achieved with a daily dose of 10 grams 1% ANDROGEL®, about 5.4 grams of the 1% testosterone gel were needed or about 3.7 grams of 2% wt testosterone gel of the invention were needed.

Figure 13:
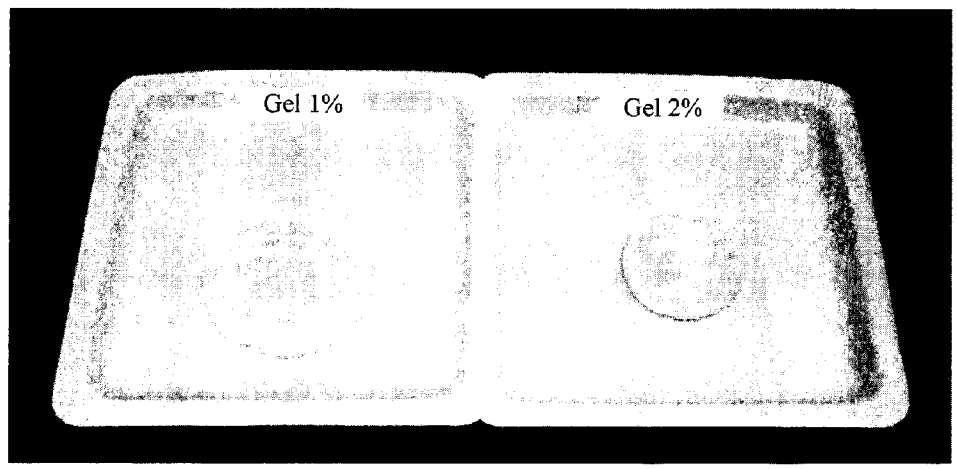
FIG. 13 is a demonstration of the volume amount of a 2% wt testosterone formulation compared to a 1% wt testosterone formulation having similar testosterone plasma levels (left: 5.4 grams of testosterone 1% gel, deemed therapeutically equivalent to 10 grams ANDROGEL; right: 3.7 grams of a testosterone 2% gel, also deemed therapeutically equivalent to 10 grams ANDROGEL) (see Example 7).

FIG. 13 demonstrates the difference in the volume amount of transdermal testosterone formulation to be applied when using 1% testosterone gel compared to 2% wt testosterone gel.

The above data show that for a given daily dose of testosterone (e.g. 50 mg), daily administration of the 2% wt testosterone gel provides superior advantages over the use of the 1% wt testosterone gel, as the former leads to smoother plasma profiles together with a lower formulation dose and reduced dosing frequency, hence to an improved activity/safety profile for the patient in need thereof.

The formulations of the invention thus demonstrate an advantageous once daily administration volume. Such advantageous administration volume results in a shortened administration time, in a decrease in the amount of unabsorbed testosterone left on the skin of a subject, in a decreased exposure of the surroundings to the testosterone, and to a decreased exposure of the testosterone to degradation processes. Accordingly, formulations of the invention were shown to deliver therapeutic amounts of testosterone by a convenient and simplified dosing regimen.

Example 8

A Phase 2 Open-Label, Sequential Dose Escalation Study to Evaluate the Efficacy, Pharmacokinetics and Safety of Three Volumes of Transdermal Testosterone Gel Formulation Comprising 2% Testosterone in Hypogonadal Males The primary objectives of the study were to determine the pharmacokinetics of total testosterone after 10 days of treatment with each of three volumes—1.25, 2.50 and 3.75 mL—of transdermal testosterone gel formulation comprising 2% testosterone (produced essentially as described in Example 1) in hypogonadal males and to determine if the treatments restore the testosterone to the normal male physiologic range (which is about 298 to 1,043 ng/dL for total testosterone).

The three volumes—1.25, 2.50 and 3.75 mL—of transdermal testosterone gel formulation comprising 2% testosterone are respectively equivalent to 23, 46 and 70 mg of testosterone and to 1.15, 2.3 and 3.45 grams of gel.

The secondary pharmacokinetic objectives of the study were to determine the kinetics of a single dose of 2.50 mL of transdermal testosterone gel formulation comprising 2% testosterone (produced essentially as described in Example 1) applied to three different locations: thigh, abdomen, and shoulder.

In the first part of the study, subjects received sequential single applications of 2.50 mL gel applied to the inner thigh, abdomen, and shoulder/upper arm. Plasma samples were collected at intervals (pre-dose and at 2, 4, 6, 8, 10, and 24 hr post-dose) up to 24 hr for pharmacokinetic analysis. Following the first two single doses, there were 5- to 7-day washout periods, but only a 24-hr period after the third dose before the start of the second part of the study.

In the second part of the study, multiple daily doses of 1.25 mL were applied to the shoulder/upper arm for 10 days, followed by 2.50 mL for 10 days, followed by 3.75 mL for 10 days, with no washout between dose levels. Samples for pharmacokinetic analysis were collected on the 10$^{th}$ day of each dose level. For each of the pharmacokinetic profiles, blood samples were collected pre-dose and at 2, 4, 6, 8, 10, and 24 hr post-dose.

Twenty subjects entered and completed both parts of the study.

Four analytes were measured: total testosterone, free testosterone, Dihydrotestosterone (DHT), and sex hormone binding globulin (SHBG). For total and free testosterone and DHT, $C_{max}$, $T_{max}$, $C_{min}$, $T_{min}$, $AUC_{0-24}$, and $C_{ave}$ were calculated using non-compartmental pharmacokinetic models. For SHBG, $C_{ave}$ was calculated.

Total testosterone in serum was determined by high pressure liquid chromatography with tandem mass spectrometry detection (LC/MS/MS). The percent of free testosterone was determined by equilibrium dialysis, and the concentration of free testosterone in the serum was calculated using the concentration of total testosterone and the percentage of free testosterone. The serum concentrations of the testosterone metabolite, DHT, were determined by LC/MS/MS. The concentrations of SHBG were determined by an immunoradiometric assay (IRMA).

The results for the single applications of 2.50 mL to the thigh, abdomen, and shoulder are shown in Table 9.

TABLE 9

| | Pharmacokinetic Parameters for Single Applications | | | | | |
|---|---|---|---|---|---|---|
| | $C_{max}$ Mean ± SD | $T_{max}$ (hr) Median | $C_{min}$ Mean ± SD | $T_{min}$ (hr) Median | $AUC_{0-24}$ Mean ± SD | $C_{ave}$ Mean ± SD |
| | Total Testosterone (units of ng/dL for $C_{max}$, $C_{min}$, and $C_{ave}$, units of ng · hr/dL for $AUC_{0-24}$) | | | | | |
| Thigh | 519 ± 171 | 24.0 | 304 ± 81 | 5.0 | 9,473 ± 2,306 | 395 ± 96 |
| Abdomen | 451 ± 157 | 9.0 | 268 ± 61 | 0 | 8,917 ± 2,925 | 372 ± 122 |
| Shoulder | 926 ± 737 | 11.0 | 289 ± 71 | 0 | 13,368 ± 7,162 | 557 ± 298 |
| | Free Testosterone (units of pg/mL for $C_{max}$, $C_{min}$, and $C_{ave}$, units of pg · hr/mL for $AUC_{0-24}$) | | | | | |
| Thigh | 101 ± 35 | 24.0 | 51.0 ± 20.4 | 3.0 | 1,738 ± 534 | 72.4 ± 22.2 |
| Abdomen | 96.4 ± 49.2 | 8.0 | 43.5 ± 14.4 | 5.0 | 1,639 ± 775 | 68.3 ± 32.3 |
| Shoulder | 182 ± 137 | 7.0 | 49.6 ± 18.7 | 1.0 | 2,863 ± 1,734 | 119 ± 72 |

TABLE 9-continued

| | Pharmacokinetic Parameters for Single Applications | | | | | |
|---|---|---|---|---|---|---|
| | $C_{max}$ Mean ± SD | $T_{max}$ (hr) Median | $C_{min}$ Mean ± SD | $T_{min}$ (hr) Median | $AUC_{0-24}$ Mean ± SD | $C_{ave}$ Mean ± SD |
| | DHT (units of ng/dL for $C_{max}$, $C_{min}$ and $C_{ave}$, units of ng · hr/dL for $AUC_{0-24}$) | | | | | |
| Thigh | 61.5 ± 28.2 | 10.0 | 22.9 ± 8.1 | 0 | 1,173 ± 589 | 48.9 ± 24.5 |
| Abdomen | 45.9 ± 19.1 | 8.0 | 22.8 ± 9.3 | 0 | 884 ± 407 | 36.9 ± 17.0 |
| Shoulder | 76.3 ± 53.8 | 9.0 | 22.0 ± 7.9 | 0 | 1,262 ± 758 | 52.6 ± 31.6 |
| | SHBG (units of nM for $C_{ave}$) | | | | | |
| Thigh | — | — | — | — | — | 26.3 ± 9.7 |
| Abdomen | — | — | — | — | — | 24.0 ± 8.5 |
| Shoulder | — | — | — | — | — | 25.3 ± 9.2 |

The results for multiple applications for 10 days of 1.25, 2.50, and 3.75 mL gel to the shoulder are shown in Table 10.

TABLE 10

| | Pharmacokinetic Parameters for Multiple Applications | | | | | |
|---|---|---|---|---|---|---|
| | $C_{max}$ Mean ± SD | $T_{max}$ (hr) Median | $C_{min}$ Mean ± SD | $T_{min}$ (hr) Median | $AUC_{0-24}$ Mean ± SD | $C_{ave}$ Mean ± SD |
| | Total Testosterone (units of ng/dL for $C_{max}$, $C_{min}$, and $C_{ave}$, units of ng · hr/dL for $AUC_{0-24}$) | | | | | |
| 1.25 mL | 586 ± 290 | 6.0 | 261 ± 83 | 8.0 | 9,229 ± 2,946 | 385 ± 123 |
| 2.50 mL | 907 ± 784 | 5.0 | 289 ± 111 | 5.0 | 12,113 ± 6,309 | 505 ± 263 |
| 3.75 mL | 1,258 ± 774 | 6.0 | 381 ± 174 | 7.0 | 17,633 ± 9,256 | 735 ± 386 |
| | Free Testosterone (units of pg/mL for $C_{max}$, $C_{min}$, and $C_{ave}$, units of pg · hr/mL for $AUC_{0-24}$) | | | | | |
| 1.25 mL | 134 ± 90 | 6.0 | 49.4 ± 20.2 | 7.0 | 1,766 ± 781 | 73.6 ± 32.5 |
| 2.50 mL | 203 | | 70.8 | | 2,342 | 97.6 |
| 3.75 mL | 382 ± 342 | 6.0 | 86.4 ± 57.5 | 5.0 | 4,686 ± 3,575 | 195 ± 149 |
| | DHT (units of ng/dL for $C_{max}$, $C_{min}$, and $C_{ave}$, units of ng · hr/dL for $AUC_{0-24}$) | | | | | |
| 1.25 mL | 64.4 ± 32.2 | 6.0 | 34.9 ± 15.2 | 9.0 | 1,063 ± 497 | 44.3 ± 19.9 |
| 2.50 mL | 93.3 ± 51.9 | 4.0 | 41.7 ± 18.1 | 12.0 | 1,458 ± 727 | 60.7 ± 30.3 |
| 3.75 mL | 120 ± 60 | 6.0 | 54.6 ± 24.6 | 6.0 | 1,974 ± 890 | 82.2 ± 37.1 |
| | SHBG (units of nM for $C_{ave}$) | | | | | |
| 1.25 mL | — | — | — | — | — | 22.9 ± 8.4 |
| 2.50 mL | — | — | — | — | — | 21.8 ± 7.8 |
| 3.75 mL | — | — | — | — | — | 23.6 ± 8.9 |

Note:
Due to multiple missing concentration values, individual parameters for free testosterone could not be calculated for 2.50 mL multiple applications. The values in the table for 2.50 mL were calculated using mean concentrations.

Conclusions:

Total Testosterone: For the single applications, the results for thigh and abdomen were similar. For the shoulder, the mean, median, and maximum values for $C_{max}$, $AUC_{0-24}$, and $C_{ave}$ were higher than the corresponding values for the thigh or abdomen. For multiple applications to the shoulder, mean, median, minimum and maximum values for $C_{max}$, $C_{min}$, $AUC_{0-24}$, and $C_{ave}$ increased with increasing dose. The effects of application site and dose on $C_{ave}$ were statistically significant (p<0.05).

Free Testosterone: For single applications, the results for free testosterone for the thigh and abdomen were similar. For the shoulder, the mean, median, and maximum values for $C_{max}$, $AUC_{0-24}$, and $C_{ave}$ were higher than the corresponding values for the thigh or abdomen. For multiple applications, the mean, median, and maximum values for $C_{max}$, $C_{min}$, $AUC_{0-24}$, and $C_{ave}$ increased with increasing dose. Some individual subjects showed distinct increases with dose, but other subjects did not show dose-related increases. The effects of application site and dose on $C_{ave}$ were statistically significant (p<0.05).

DHT: For single applications, $C_{max}$, $AUC_{0-24}$, and $C_{ave}$ were similar for the thigh and shoulder, with apparently lower values for the abdomen. However, there was no statistically significant effect (p=0.218) on $C_{ave}$ or $AUC_{0-24}$. $C_{min}$ was nearly identical for all three sites. The plasma concentration time profiles showed evidence of absorption and metabolism of testosterone. The mean minimum concentrations of DHT for single applications were the baseline pre-dose concentrations and the maximum concentrations were at a distinctly later time. For the multiple applications, the mean, median, and maximum values for $C_{max}$, $C_{min}$, $AUC_{0-24}$, and $C_{ave}$ increased with increasing dose. The increases in $C_{ave}$ with increasing gel volume were statistically significant (p<0.05).

SHBG: For both single and multiple applications, the values of $C_{ave}$ were similar for all sites and doses. Neither application site nor gel volume had a statistically significant effect on $C_{ave}$ (p=0.738 and 0.784, respectively).

Overall: The mean concentrations and pharmacokinetic parameters showed evidence of dose-dependent absorption of testosterone with subsequent metabolism to DHT.

The invention claimed is:

1. A transdermal or transmucosal formulation comprising:
   2% wt of testosterone,
   at least one $C_2$ to $C_4$ alkanol,
   15-30% wt polyalcohol, wherein the polyalcohol is one or more of a $C_2$ to $C_6$ alkane or $C_2$ to $C_6$ alkene, substituted with two or more hydroxyl groups, and
   monoalkyl ether of diethylene glycol,
   wherein said formulation is substantially free of long-chain fatty alcohols, long-chain fatty acids, and long-chain fatty esters.

2. The transdermal or transmucosal formulation according to claim 1, further comprising at least one of:
   gelling agent,
   neutralizing agent,
   chelating agent and
   solvent
   or any combinations thereof.

3. The formulation of claim 2, wherein the alkanol is present in an amount between about 5-50% wt, the permeation enhancer is present in an amount of between about 0.2-25% wt, the gelling agent is present in an amount between about 0.05-4% wt, the neutralizing agent is present in an amount between about 0.05-1% wt, and the chelating agent is present in an amount between about 0.001-5.0% wt.

4. The formulation of claim 1, wherein the at least one alkanol is chosen from ethanol, isopropanol n-propanol, and combinations thereof.

5. The formulation of claim 1, wherein the at least one alkanol is ethanol.

6. The formulation of claim 1, wherein the alkanol is ethanol, present in an amount of about 44.0% wt.

7. The formulation of claim 1, wherein the polyalcohol is propylene glycol.

8. The formulation of claim 7, wherein the propylene glycol is present in an amount of about 20.0% wt.

9. The formulation of claim 1, wherein the monoalkyl ether of diethylene glycol is chosen from diethylene glycol monoethyl ether, diethylene glycol monomethyl ether, and combination thereof.

10. The formulation of claim 9, wherein diethylene glycol monoethyl ether is present in an amount of 5.0% wt.

11. The formulation of claim 2, wherein the gelling agent is carbomer.

12. The formulation of claim 11, wherein the carbomer is present in an amount of 1.20% wt.

13. The formulation of claim 2, wherein the gelling agent is poly(acrylic acid), present in an amount of 1.20% wt.

14. The formulation of claim 2, wherein the neutralizing agent is triethanolamine.

15. The formulation of claim 14, wherein the triethanolamine is present in an amount of 0.35% wt.

16. The formulation of claim 2, wherein the chelating agent is edetate disodium.

17. The formulation of claim 16, wherein the edetate disodium is present in an amount of 0.06% wt.

18. The formulation of claim 2, wherein the solvent is water.

19. A transdermal or transmucosal formulation comprising: 2% wt of testosterone, 44.0% wt of ethanol, 20.0% wt of propylene glycol, and 5.0% wt of diethylene glycol monoethyl ether, wherein said formulation is substantially free of long-chain fatty alcohols, long-chain fatty acids, and long-chain fatty esters.

20. A transdermal or transmucosal formulation comprising: 2% wt of testosterone, 44.0% wt of ethanol, 20.0% wt of propylene glycol, 5.0% wt of diethylene glycol monoethyl ether, 1.20% wt of carbomer, 0.35% wt of triethanolamine, 0.06% wt of edetate disodium and water wherein said formulation is substantially free of long-chain fatty alcohols, long-chain fatty acids, and long-chain fatty esters.

21. A transdermal or transmucosal formulation consisting of 2% wt of testosterone, 44.0% wt of ethanol, 20.0% wt of propylene glycol, 5.0% wt of diethylene glycol monoethyl ether, 1.20% wt of carbomer, 0.35% wt of triethanolamine, 0.06% wt of edetate disodium and water.

22. The formulation of claim 1, wherein the formulation is in the form chosen from a gel, lotion, cream, spray, aerosol, ointment, emulsion, suspension, liposomal system, lacquer, patch, bandage, buccal tablet, sublingual tablet, suppository, vaginal dosage form or occlusive dressing.

23. The formulation claim 22, wherein the form is a gel.

24. The formulation claim 1, wherein the formulation is adapted for transdermal or transmucosal administration according to a schedule having a periodicity chosen from once to five times daily dosing, once-weekly dosing or bi-weekly dosing.

25. The formulation of claim 1, wherein the formulation is adapted for a once daily transdermal or transmucosal administration.

26. The formulation of claim 1, wherein the formulation is adapted for a once daily transdermal or transmucosal administration to the abdomen of a mammal in need thereof.

27. The formulation of claim 1, wherein the formulation is adapted for a once daily transdermal or transmucosal administration to the upper arm of a mammal in need thereof.

28. A method for administering testosterone to a mammal in need thereof comprising:
   transdermally administering to a skin or mucosal membrane of a mammal a formulation according to claim 1.

29. A method of treating a disease or disorder associated with reduced endogenous testosterone production comprising:
   transdermally administering to a skin or mucosal membrane of a mammal a formulation according to claim 1.

30. The method according to claim 28 or 29, wherein said mammal is a male.

31. A method of treating a disease or disorder associated with reduced endogenous testosterone production in a male subject comprising:
   transdermally administering to a skin or mucosal membrane of a male subject a formulation comprising: 1-2% wt of testosterone, $C_2$ to $C_4$ alkanol, 20.0% wt of propylene glycol, and monoalkyl ether of diethylene glycol, wherein said formulation is substantially free of long-chain fatty alcohols, long-chain fatty acids, and long-chain fatty esters.

32. A method of treating a disease or disorder associated with reduced endogenous testosterone production in a male subject comprising:
   transdermally administering to a skin or mucosal membrane of a male subject a formulation comprising: 1-2% wt of testosterone, $C_2$ to $C_4$ alkanol, 20.0% wt of propylene glycol, monoalkyl ether of diethylene glycol, gelling agent, neutralizing agent, chelating agent and solvent, wherein said formulation is substantially free of long-chain fatty alcohols, long-chain fatty acids, and long-chain fatty esters.

33. A method of treating a disease or disorder associated with reduced endogenous testosterone production in a male subject comprising:
   transdermally administering to a skin or mucosal membrane of a male subject a formulation comprising 1-2% wt of testosterone, 44% wt of ethanol, 20.0% wt of propylene glycol, 5% wt of monoethyl ether of diethylene glycol, 1.20% wt of carbomer, 0.35% wt of triethanolamine, 0.06% wt of edetate disodium and water wherein the formulation is substantially free of long-chain fatty alcohols, long-chain fatty acids, and long-chain fatty esters.

34. A method of treating a disease or disorder associated with reduced endogenous testosterone production in a male subject comprising:

transdermally administering to a skin or mucosal membrane of a male subject a formulation consisting of 1-2% wt of testosterone, 44% wt of ethanol, 20.0% wt of propylene glycol, 5% wt of monoethyl ether of diethylene glycol, 1.20% wt of carbomer, 0.35% wt of triethanolamine, 0.06% wt of edetate disodium and water.

35. The method according to claim 29, wherein the disease or disorder associated with reduced endogenous testosterone production is hypogonadism.

36. The method according to claim 29, further comprising administering another treatment.

37. A kit comprising at least one container comprising a formulation according to claim 1, and instructions for use thereof.

38. A kit according to claim 37, wherein said container is adapted for dispensing a predetermined measured amount of the formulation.

* * * * *